(12) United States Patent
Smith et al.

(10) Patent No.: US 7,389,025 B2
(45) Date of Patent: Jun. 17, 2008

(54) COUPLING LIGHT INTO MICRORESONATORS

(75) Inventors: Terry L. Smith, Roseville, MN (US);
Barry J. Koch, Woodbury, MN (US);
Michael A. Haase, St. Paul, MN (US);
Jun-Ying Zhang, St. Paul, MN (US);
Robert W. Wilson, Austin, TX (US);
Xudong Fan, Columbia, MO (US)

(73) Assignee: 3M Innovative Properties Company, St. Paul, MN (US)

( * ) Notice: Subject to any disclaimer, the term of this patent is extended or adjusted under 35 U.S.C. 154(b) by 210 days.

(21) Appl. No.: 11/277,769

(22) Filed: Mar. 29, 2006

(65) Prior Publication Data

US 2008/0008418 A1 Jan. 10, 2008

(51) Int. Cl.
*G02B 6/26* (2006.01)

(52) U.S. Cl. .......................... 385/39; 385/12; 385/40; 385/41

(58) Field of Classification Search .................. 385/12, 385/39
See application file for complete search history.

(56) References Cited

U.S. PATENT DOCUMENTS

| | | | |
|---|---|---|---|
| 3,833,284 A | 9/1974 | Kaminow et al. | |
| 4,715,672 A | 12/1987 | Duguay et al. | |
| 5,077,822 A | 12/1991 | Cremer | |
| 6,389,197 B1 | 5/2002 | Iltchenko et al. | |
| 6,490,039 B2 | 12/2002 | Maleki et al. | |
| 6,507,684 B2 | 1/2003 | Tapalian et al. | |
| 6,512,866 B1 | 1/2003 | Fan et al. | |
| 6,583,399 B1 | 6/2003 | Hunziker et al. | |
| 6,594,425 B2 | 7/2003 | Tapalian et al. | |
| 6,657,731 B2 | 12/2003 | Tapalian et al. | |
| 6,668,111 B2 | 12/2003 | Tapalian et al. | |
| 6,781,696 B1 | 8/2004 | Rosenberger et al. | |
| 6,795,481 B2 | 9/2004 | Maleki et al. | |
| 6,865,317 B2 | 3/2005 | Vahala et al. | |
| 6,888,987 B2 | 5/2005 | Sercel et al. | |
| 6,891,996 B2 | 5/2005 | Sercel et al. | |
| 6,891,997 B2 | 5/2005 | Sercel et al. | |
| 6,895,135 B2 | 5/2005 | Kaneko et al. | |
| 6,901,101 B2 | 5/2005 | Frick | |
| 2002/0018611 A1 | 2/2002 | Maleki et al. | |

(Continued)

FOREIGN PATENT DOCUMENTS

GB 2 293 883 4/1996

(Continued)

OTHER PUBLICATIONS

Armani, D.K., et al; "Ultra-High-Q Toroid Microcavity on a Chip", Letters to Nature, *Nature* (Feb. 27, 2003); vol. 421, Nature Publishing Group; pp. 925-928.

(Continued)

*Primary Examiner*—Frank G. Font
*Assistant Examiner*—Eric Wong
(74) *Attorney, Agent, or Firm*—Robert S. Moshrefzaden

(57) ABSTRACT

An optical microresonator device is described including an optical waveguide and an optical microresonator positioned so as to optically couple to the waveguide. The waveguide includes a core and a metal cladding layer on at least part of one boundary of the core.

17 Claims, 11 Drawing Sheets

U.S. PATENT DOCUMENTS

| | | |
|---|---|---|
| 2002/0041730 A1 | 4/2002 | Sercel et al. |
| 2002/0044739 A1 | 4/2002 | Vahala et al. |
| 2002/0068018 A1 | 6/2002 | Pepper et al. |
| 2002/0079453 A1 | 6/2002 | Tapalian et al. |
| 2002/0094150 A1* | 7/2002 | Lim et al. .................... 385/15 |
| 2002/0097401 A1 | 7/2002 | Maleki et al. |
| 2002/0172457 A1 | 11/2002 | Tapalian et al. |
| 2002/0192680 A1 | 12/2002 | Chan et al. |
| 2003/0082237 A1 | 5/2003 | Cha et al. |
| 2004/0023396 A1 | 2/2004 | Boyd et al. |
| 2004/0091212 A1 | 5/2004 | Strecker et al. |
| 2004/0120638 A1 | 6/2004 | Frick |
| 2004/0146431 A1 | 7/2004 | Scherer et al. |
| 2004/0196465 A1 | 10/2004 | Arnold et al. |
| 2005/0035278 A1 | 2/2005 | Margalit et al. |
| 2005/0077513 A1 | 4/2005 | Fan et al. |
| 2005/0078731 A1 | 4/2005 | Fan et al. |
| 2005/0105868 A1 | 5/2005 | Arakida |
| 2005/0111309 A1 | 5/2005 | Peng |
| 2005/0147372 A1 | 7/2005 | Bourdelais et al. |
| 2005/0263679 A1 | 12/2005 | Fan et al. |
| 2005/0265658 A1 | 12/2005 | Fan et al. |

FOREIGN PATENT DOCUMENTS

| | | |
|---|---|---|
| GB | 2 387 130 | 10/2003 |
| WO | WO 01/40757 A2 | 6/2001 |
| WO | WO 01/67565 A1 | 9/2001 |
| WO | WO 01/85341 | 11/2001 |
| WO | WO 02/13337 A1 | 2/2002 |
| WO | WO 02/16986 A1 | 2/2002 |
| WO | WO 2004/038370 A2 | 5/2004 |

OTHER PUBLICATIONS

Blair et al., "Resonant-Enhanced Evanescent-Wave Fluorescence Biosensing with Cylindrical Optical Cavities", Applied Optics, vol. 40, No. 4, Feb. 1, 2001, pp. 570-582.

Boyd et al., "Sensitive Disk Resonator Photonic Biosensor", Applied Optics, vol. 40, No. 31, Nov. 1, 2001, pp. 5742-5747.

Burlak, G., et al; "Electromagnetic Eigenoscillations and Fields in a Dielectric Microsphere with Multilayer Spherical Stack", Optics Communications (Jan. 1, 2001); vol. 187, Elsevier Science B.V.; pp. 91-105.

Burlak, G., et al; "Electromagnetic Oscillations in a Multilayer Spherical Stack", Optics Communications, (Jun. 1, 2000); vol. 180; Elsevier Science B.V.; pp. 49-58.

Burlak, G., et al; "Transmittance and Resonance Tunneling of the Optical Fields in the Microspherical Metal-Dielectric Structures", Optics Communications (May 15, 2002); vol. 206, Elsevier Science B.V.; pp. 27-37.

Chan, S., et al; "Identification of Gram Negative Bacteria Using Nanoscale Silicon Microcavities", Communications to the Editor, Journal of American Chemical Society (Nov. 2001); vol. 123, pp. 11797-11798.

Chan, S., et al; "Nanoscale Silicon Microcavities for Biosensing", Materials Science and Engineering C (2001); vol. 15, Elsevier Scieice B.V.; pp. 277-282.

Coffer et al., "Strategies Toward the Development of Integrated Chemical Sensors Fabricated from Light Emitting Porous Silicon", Proceedings of the SPIE, vol. 3226, 1997, pp. 168-179.

Crisan et al., "Sol-Gel Preparation of Thin Films for Integrated Optics", 10th International Symposium on Electron Devices for Microwave and Optoelectronic Applications, Nov. 18-19, 2002, Manchester, UK., pp. 205-210.

Garmire , E, et al, "Propagation Losses in Metal-film-substrate Optical Waveguides", Journal of Quantum Electronics, vol. QE-8, No. 10, Oct. 1972, pp. 763-766.

Johnson, B.R.; "Theory of Morphology-Dependent Resonances: Shape Resonances and Width Formulas", J. Opt. Soc. Am. A (Feb. 1993); vol. 10, No. 2; pp. 343-352.

Kakarantzas, G., et al; "Miniature All-Fiber Devices Based in $CO_2$ Laser Microstructuring of Tapered Fibers", Optics Letters (Aug. 1, 2001); vol. 26, No. 15; pp. 1137-1139.

Kaminow, I.P., et al., "Metal-Clad Optical Waveguides: Analytical and Experimental Study", Applied Optics, vol. 13, (1974), pp. 396.

Knight, J.C., et al; "Mapping Whispering-Gallery Modes in Microspheres with a Near-Field Probe", Optics Letters (Jul. 15, 1995); vol. 20, No. 14; pp. 1515-1517.

Krioukov et al., "Sensor Based on an Integrated Optical Microcavity", Optical Letters, vol. 27, No. 7, Apr. 1, 2002, pp. 512-514.

Krioukov, E., et al; "Integrated Optical Microcavities for Enhanced Evanescent-Wave Spectroscopy", Optical Letters, (Sep. 1, 2002); vol. 27, No. 17; pp. 1504-1506.

Laine, J.-P., et al; "Acceleration Sensor Based on High-Q Optical Microsphere Resonator and Pedestal Antiresonant Reflecting Waveguide Coupler", Sensors and Actuators A (2001); vol. 93; Elsevier Science B.V.; pp. 1-7.

Laine, J.-P., et al; "Microsphere Resonantor Mode Characterization by Pedestal Anti-Resonant Reflecting Waveguide Coupler", IEEE Photonics Technology Letters (Aug. 2000); vol. 12, No. 8; pp. 1004-1006.

Little, B.E., et al; "Pedestal Antiresonant Reflecting Waveguides for Robust Coupling to Microsphere Resonators and for Microphotonic Circuits", Optics Letters (Jan. 1, 2000); vol. 25, No. 1; pp. 73-75.

Lugo, J.E., et al; "Porous Silicon Multilayer Structures: A Photonic Band Gap Analysis", Journal of Applied of Physics (Apr. 15, 2002); vol. 91, No. 8; pp. 4966-4972.

Luk, J.M.C., et al; "Rapid and Sensitive Detection of Salmonella (O : 6,7) by Immunomagnetic Monoclonal Antibody-Based Assays", Journal of Immunological Methods (1991); vol. 137; pp. 1-8.

Martin, A.L., et al; "Replica-Molded High-Q Polymer Microresonators", Optics Letters (Mar. 15, 2004); vol. 29, No. 6; pp. 533-535.

Otto, A., et al, "Modification of the Total Reflection Modes in a Dielectric Film by One Metal Boundary", Optics Communications, vol. 3, No. 4, Jun. 1971, pp. 254-258.

Pettipher, G.L., et al; "Rapid Enumeration of Microorganisms in Foods by the Direct Epifluorescent Filter Technique", Applied and Environmental Microbiology (Oct. 1982); vol. 44, No. 4; pp. 809-813.

Pipino et al., "Evanescent Wave Cavity Ring-Down Spectroscopy with a Total-Internal-Reflection Minicavity", Review of Scientific Instruments, American Institute of Physics, vol. 68, No. 8, Aug. 8, 1997, 2978-2989.

Plowman, T.E., et al; "Femtomolar Sensitivity Using a Channel-Etched Thin Film Waveguide Fluoroimmunosensor", Biosensors & Bioelectronics (1996); Elsevier Science Ltd.; vol. 11, No. 1/2; pp. 149-160.

Popescu, A., et al; "The Gram Stain after than a Century", Biotechnic and Histochemistry (1996); vol. 71, No. 3; pp. 145-151.

Reisinger, A, "Attenuation Properties of Optical Waveguides with a Metal Boundary", Appl. Phys. Lett., vol. 23, No. 5, Sep. 1, 1973, pp. 237-239.

Shibata et al., "Laser Emission from Dye-Doped Organic-Inorganic Particles of Mircocavity Structure", Journal of Sol-Gel Science and Technology, vol. 8, 1997, pp. 959-964.

Suematsu, et al, "Fundamental Transverse Electric Field (TE0) Mode Selection for Thin-film Asymmetric Light Guides", Appl. Phys. Lett., vol. 21, No. 6, Sep. 15, 1972, pp. 291-293.

Spillane, S.M., et al; "Ultralow-Threshold Raman Laser Using a Spherical Dielectric Microcavity", Letters to Nature, Nature (Feb. 7, 2002); vol. 415, Macmillan Magazines Ltd., pp. 621-623.

Sumetsky, M., "Whispering-Gallery-Bottle Microcavities: the Three-Dimensional Etalon", Optics Letters (Jan. 1, 2004); vol. 29, No. 1; pp. 8-10.

Tapalian, C., et al; "High-Q Silica Microsphere Optical Resonator Sensors Using Stripline-Pedestal Anti-Resonant Reflecting Optical Waveguide Couplers"; Proceedings from SPIE, Photonics West 2003 (Jan. 25-31, 2003); vol. 4969; Laser Resonators and Beam Control VI; Item 4969-30; pp. 11-22.

Tien, P, et al, "Novel Metal-clad Optical Components and Method of Isolating High-index Substrates for Forming Integrated Optical Circuits", Appl. Phys. Lett., vol. 27, No. 4, Aug. 15, 1975, pp. 251-253.

Tortorello, M.L., et al; "Antibody-Direct Epifluorescent Filter Technique for Rapid, Direct Enumeration of *Escherichia coli* O157:H7 in Beef", *Applied and Environmental Microbiology* (Oct. 1994); vol. 60, No. 10; pp. 3553-3559.

Tortorello, M.L., et al; "Rapid Identification of *Escherichia coli* O157:H7 in Bovine Feces Using the Antibody-Direct Epifluorescent Filter Technique (Ab-DEFT)", *Veterinary Microbiology* (1996); vol. 51; pp. 343-349.

Vernooy, D.W., et al; "High-Q Measurements of Fused-Silica Microspheres in the Near Infrared", *Optics Letters* (Feb. 15, 1998); vol. 23, No. 4; pp. 247-249.

Vollmer, F., et al; "Protein Detection by Optical Shift of a Resonant Microcavity", *Applied Physics Letters* (May 27, 2002); vol. 80, No. 21; pp. 4057-4059.

Wark et al., "Incorporation of Organic Dye Molecules in Nanoporous Crystals for the Development of Hexagonal Solid State Microlasers", *Proceedings of the SPIE*, vol 4456, 2001, pp. 57-67.

Yoneyama et al., "Nonradiative Dieletric Waveguide Circuit Components", *International Journal of Infrared and Millimeter Waves*, vol. 4, No. 3 (1983), p. 439-449.

Yunfeng et al., "Chemical Sensors Based on Hydrophobic Porous Sol-Gel Films and ATR-FTIR Spectroscopy", *Sensors and Actuators B, Elsevier Sequoia S.A.*, vol. B36, No. 1, 2, and 3, Oct. 1996, pp. 517-521.

XU, G.; "Gram Stain", University of Pennsylvania Health System [on line]; [available on the internet on Oct. 31, 1997]; [retrieved from the internet on Dec. 15, 2004]; URL <http://www.uphs.upenn.edu/bugdrug/antibiotic_manual/gram.html>; pp. 10.

Chan, S., et al. "Porous Silicon Microcavities for Biosensing Applications," *Physical Status Solid*, vol. 182, (2000) pp. 541-546.

De Stefano, L., et al., "Optical Sensing of Flammable Substances Using Porous Silicon Microcavities," *Materials Science and Engineering*, vol. 100, Jul. 25, 2003, pp. 271-274.

Mulloni, V., et al. "Porous Silicon Microcavities as Optical Chemical Sensors," *Applied Physics Letters*, vol. 76, No. 18, May 1, 2000, pp. 2523-2525.

* cited by examiner

COUPLING LIGHT INTO MICRORESONATORS

FIELD OF THE INVENTION

The present invention is directed generally to optical devices based on microresonators coupled to waveguides.

BACKGROUND OF THE INVENTION

Dielectric cavity optical resonators have attracted increasing attention in sensing applications, including biosensing. Typically these resonators consist of either microspheres, or of planar-waveguide-based disk or ring cavities. The size of these types of resonators typically ranges from approximately 20 microns to a few millimeters for microspheres and from 5 microns to several hundreds of microns for ring- or disk-shaped resonators. Such small spheres and ring- or disk-shaped resonators are often referred to as microresonators.

In the most common configuration in microresonator-based sensors, a microresonator is placed in close proximity to an optical waveguide such as optical fiber whose geometry has been specifically tailored, for example, tapered or etched to a size of 1-5 microns. The tapering modifications to the waveguide result in there being a substantial optical field outside the waveguide, and thus light can couple into the microresonator and excite its eigenmodes. These eigenmodes may be of various types, depending upon the resonant cavity geometry. For spherical and disk cavities, the modes of interest for sensing applications are usually the so-called "whispering gallery modes" (WGMs), which are traveling waves confined close to the surface of the cavity. Since the WGMs are confined near the surface, they are well-suited to coupling with analytes on or near the sphere surface. FIG. 2 schematically illustrates the WGM 202 electric field distribution for light propagating within a planar disk microresonator cavity 210. The field intensity, E, is schematically illustrated in FIG. 2 for the WGM 202 along the cross-section line A-A'.

For ring cavities based on single-mode waveguides, the modes are those of the single-transverse-mode channel waveguide, under the constraint that the path traversed corresponds to an integral number of wavelengths. Other cavity geometries, such as Fabry-Perot resonators using single-mode waveguides with Bragg grating reflectors, or multimode rectangular cavities, have familiar standing-wave resonances as their eigenmodes.

When microresonators made with low loss materials and with high surface reflectivity and quality are used, the loss of light confined in the resonant modes is very low, and extremely high quality factors, also known as Q-factors, can be achieved, as high as $10^9$. Due to the high Q-factor, the light can circulate inside the resonator for a very long time, thus leading to a very large field enhancement in the cavity mode, and a very long effective light propagation path. This makes such devices useful for non-linear optical and sensing applications. In sensing applications, the samples to be sensed are placed on or very near the resonator's surface, where they interact with the evanescent portion of the resonant electric field available outside the microresonator. Due to the enhanced field and the increased interaction length between the light and samples, the microresonator-based optical sensors feature high sensitivity and/or a low detection limit.

In the most-commonly-pursued configuration, in which a microsphere resonator is coupled to a tapered optical fiber, there are practical difficulties associated with realizing efficient and stable coupling. First, in order to make the optical field in the fiber core available outside the fiber's surface, the fiber must be tapered to a few microns in diameter. This commonly results in a relatively long (a few cm) and fragile tapered region. Second, the relative position of the microsphere and the fiber taper must be held constant to within a few nanometers if the optical coupling and the Q-factor are to remain constant. This is difficult with a free sphere and tapered fiber.

In another configuration commonly used to couple with microspheres, an angle polished fiber is put into contact with the microsphere. In this case the problems associated with the fragility of the fiber taper are overcome, but there are still significant difficulties in positioning the microsphere properly on the fiber tip. Furthermore, light which is not coupled into the microsphere, representing the so-called "through port" signal, is not confined to a fiber and is therefore difficult to collect and analyze.

There is a need for improved methods and structures for coupling a waveguide to a microresonator.

SUMMARY OF THE INVENTION

An optical microresonator device is described, including an optical waveguide and an optical microresonator positioned so as to optically couple to the waveguide. The waveguide includes a core and a metal cladding layer on at least a part of one boundary of the core.

The invention may be more completely understood by considering the detailed description of various embodiments of the invention that follows in connection with the accompanying drawings.

Figure 1A:
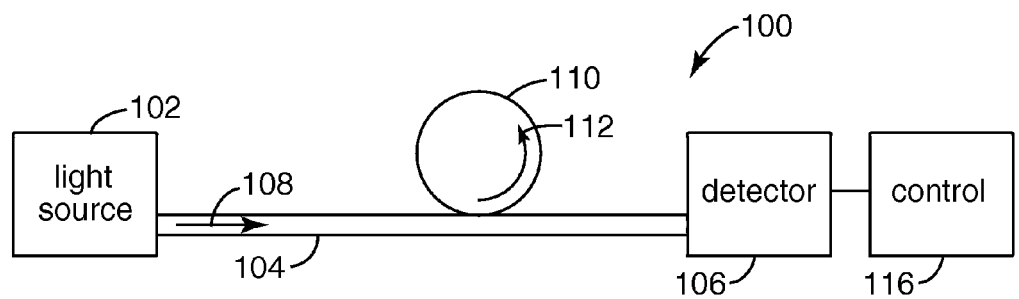
FIGS. 1A, 1B and 1C schematically illustrate embodiments of a microresonator-based device.

While the invention may be modified in many ways, specifics have been shown by way of example in the drawings and will be described in detail. It should be understood, however, that the intention is not to limit the invention to the particular embodiments described. On the contrary, the intention is to cover all modifications, equivalents, and alternatives following within the scope and spirit of the invention as defined by the claims.

DETAILED DESCRIPTION OF THE PREFERRED EMBODIMENT

The present invention is applicable to optical microresonator devices, in particular where an optical waveguide is coupled to an optical microresonator. Devices based on the coupling of a waveguide to one or more microresonators are particularly useful in the context of sensors, filters, telecommunications devices, and microlasers.

Metal clad waveguides are known, but have not previously been seen by the inventors to be coupled to a microresonator. Historically, perhaps a metal clad waveguide has not been suggested for coupling to a microresonator because metal claddings have a higher degree of optical loss than other cladding structures. It has been discovered that by using a metal clad waveguide with an optical microresonator, it is possible to efficiently couple light from a metal-clad waveguide to a microresonator with an acceptable amount of loss, and achieve many other benefits with some embodiments. More of these benefits will be described herein.

The metal cladding layer is positioned in different locations in different embodiments. The waveguide core outer surfaces define boundaries of the waveguide core. The metal cladding layer is on at least a part of one boundary of the core. In some embodiments, the metal cladding is present on the waveguide core only along a section of core proximate to the resonator. The metal cladding causes the shape of the optical modes of the waveguide to be modified (see I. P. Kaminow et al, Metal-Clad Optical Waveguides: Analytical and Experimental Study, Applied Optics, Vol 13, page 396 (1974)), and can increase the strength of the electric field that is present on the opposite boundary of the dielectric core from the metal. When the metal cladding is placed on the boundary of the core opposite the resonator, this enhancement of the field strength allows the strength of coupling to the resonator to be increased over what can be achieved with a conventional dielectric cladding. Alternatively, the gap between the waveguide and resonator can be increased (to make the gap easier to fabricate) while maintaining adequate coupling.

Metals that achieve a significant shift of the mode to promote resonator coupling, but do not at the same time too strongly increase the loss of the waveguide are those that have a large value of the imaginary part of their refractive index "k" at the wavelength of operation. Examples of metals with large k values at visible and near infrared wavelengths are aluminum, gold, indium, silver, rhodium, sodium, iridium, magnesium, copper, rhenium, lead, molybdenum, platinum, zinc, nickel, strontium, niobium, tantalum, ytterbium, osmium, cobalt, iron, and vanadium.

This approach is primarily of benefit for the case of the transverse electric "TE" polarized fundamental mode, where the electric field is parallel to the metal surface. In the case of transverse magnetic "TM" polarized modes (where the electric field is perpendicular to the metal surface), the presence of the metal layer results in the fundamental mode being the "plasmon" mode where the electric field is concentrated near the metal surface, and is thus not available for coupling to a resonator positioned at the opposite side of the core from the metal. Enhanced coupling between higher-order TM modes and resonators can potentially be achieved, but generally the propagation loss of the higher order TM modes is higher than TE modes, and thus the use of this approach in device designs is less attractive.

First, we will describe examples of microresonator-waveguide systems generally and how they are used as sensors, in order to provide context for the discussion of the coupling systems. Then different configurations and embodiments of a metal clad waveguide optically coupled to a microresonator will be described, along with advantages of such systems. Finally, modeling and experimental results will be summarized.

Microcavity-Waveguide Systems

An example of a microcavity-waveguide device 100 is schematically illustrated in FIG. 1A. A light source 102 directs light along a waveguide 104 to a detector unit 106. The microresonator 110 is optically coupled to the waveguide 104. Light 108 from the light source 102 is launched into the waveguide 104 and propagates towards the detector unit 106. The microresonator 110 evanescently couples some of the light 108 out of the waveguide 104, and the out-coupled light 112 propagates within the microresonator 110. Both the coupling out of the waveguide 104 and the intensity of light 112 in the micro-cavity are maximized at one or more of the resonant frequencies of the microresonator 110.

The light source 102 may be any suitable type of light source. For increased efficiency and sensitivity, it is advantageous that the light source produces light that is efficiently coupled into the waveguide 104, for example the light source may be a laser such as a laser diode, or may be a light emitting diode. It is often advantageous that the light source produce a narrow spectrum that is tunable, so the wavelength can be scanned to probe the resonances of the microcavity. The light source 102 generates light 108 at a desired wavelength, or wavelength range. For example, where the microresonator is used in a sensor, the light source 102 generates light at a wavelength that interacts with the species being sensed. The species being sensed is typically located in proximity to the surface of the microresonator 110 so that the light propagating in the resonator interacts with the species being sensed. The light source 102 may also comprise a lamp, along with suitable optics for coupling light from the lamp into the waveguide 104.

Description of Microcavity-Waveguide Systems used as Sensors

There are several approaches to using the microcavity-waveguide system as a sensor. The choice of approach is determined by a variety of considerations, including the chemistry of the analyte to be detected, the time available for detection, the sample preparation technology, etc.

In one approach, detection is based on monitoring the intensity or wavelength of the light 108 that travels from the microresonator 110 to the detector 106. This approach is based on the fact that when analyte molecules come in contact with the resonator surface and thus enter the evanescent field of the waveguide mode, they can alter the effective refractive index of the mode, and thus its equivalent path length. This results in a shift of the resonant frequency of the resonator. The shift in the resonant frequency can be detected either by scanning the input wavelength and monitoring the resulting intensity profile, or by holding the input wavelength constant (but near a resonance) and detecting the change in the intensity of light reaching the detector 106. This approach has the benefit of being "label free", in that no taggant need be attached to the analyte in order to induce the signal change when the analyte is proximal to the resonator.

In an alternate approach when the device 100 is used as a fluorosensor, the light propagating within the microresonator 110 is absorbed by a fluorescent molecule, such as a fluorescent dye, that is in the proximity of the microresonator surface. This dye is associated with an analyte to serve as a marker that indicates the presence of the analyte. In a more specific example, the surface of the microresonator may be functionalized with antibodies specific to a desired analyte antigen. The analyte antigen molecules, conjugated with a fluorescent dye as part of the sample preparation step, are introduced to the sensor device 100. The antigen molecules bind to the antibody molecules on the microresonator 110, thus holding the fluorescent dye molecules sufficiently close to the microresonator 110 that the light circulating within microresonator 110 evanescently couples to the fluorescent molecules. The absorbed light excites the fluorescent molecules and the molecules subsequently fluoresce at a wavelength different from the excitation wavelength. Detection of the fluorescent light confirms the presence of the analyte antigen.

In another example of a fluorosensor, the analyte antigen molecules are not conjugated with a fluorescent dye, but are allowed to bind to the antibodies attached to the microresonator surface. More antibodies, conjugated to fluorescent molecules, are subsequently introduced to the sensor, and bind to the antigen. Again, the fluorescent molecules are excited by an evanescent interaction with the light propagating within the microresonator 110, and detection of the subsequent fluorescence may be used to determine the presence and abundance of the analyte antigen.

Figure 1B:
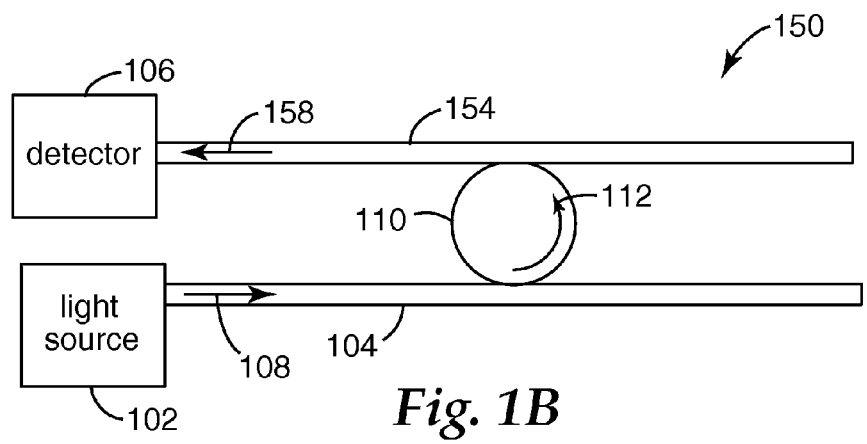
Figure 1C:
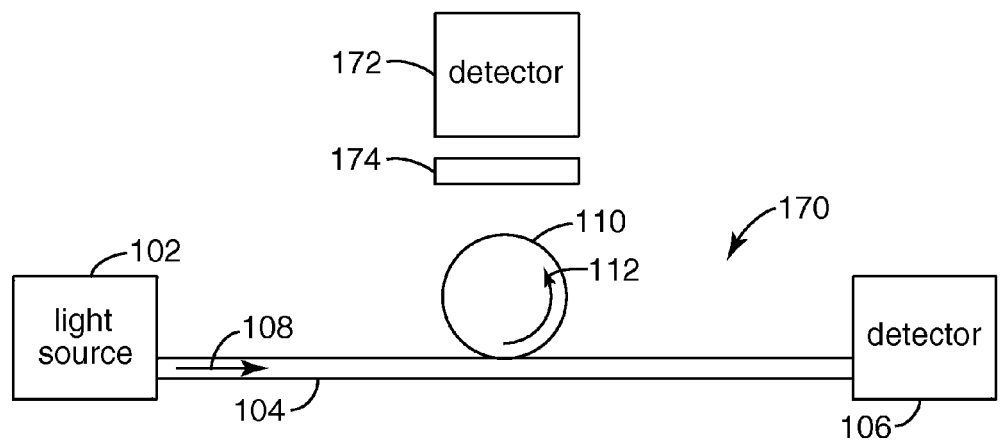
Figure 2:
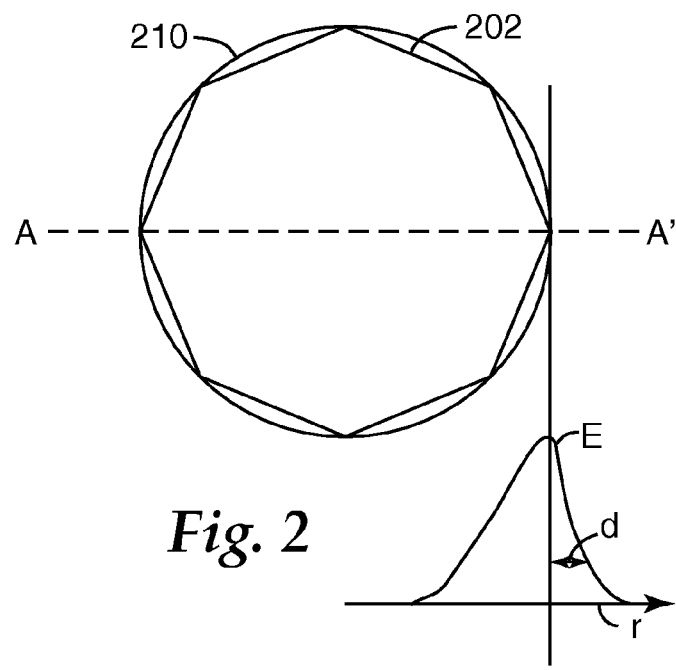
FIG. 2 schematically illustrates a ray model, and the electric field distribution for light propagating within a whispering-gallery-mode for a planar disk microresonator.

The light source 102 may direct light into a number of different waveguides, of which the waveguide 104 is one such example. According to the invention, a metal clad waveguide is used to couple light into the microresonator. In one embodiment, the waveguide 104 of FIGS. 1A-1C is a metal clad waveguide. More likely, the entire waveguide 104 is not a metal clad waveguide. Instead, a dielectric clad waveguide can couple to a metal clad waveguide near the point of optically coupling with the microresonator. The remainder of the waveguide 104 may be any suitable type of waveguide and may be, for example, a planar waveguide or a channel waveguide formed in or on a substrate, such as a waveguide formed in a silica substrate. The waveguide 104 may also be an optical fiber.

The detector unit 106 includes a light detector, for example a photodiode or photomultiplier, to detect light. The detector unit 106 may also include a wavelength sensitive device that selects the wavelength of light reaching the light detector. The wavelength selective device may be, for example, a filter, or a spectrometer. The wavelength selective device may be tunable so as to permit the user to actively change the wavelength of light incident on the light detector.

The microresonator 110 may be positioned either in physical contact with, or very close to, the waveguide 104 so that a portion of the light 108 propagating along the waveguide 104 is evanescently coupled into the microresonator 110.

Another type of microresonator device 150 is schematically illustrated in FIG. 1B. In this device 150, light 158 from the microresonator 110 is coupled into a second waveguide 154, and propagates to the detector 106.

Another type of microresonator device 170 is schematically illustrated in FIG. 1C. In this device 170, a second detector 172 is positioned close to the microresonator 110 to detect light from the microresonator 110. The light detected by the second detector 172 does not pass to the second detector 172 via a waveguide, but rather via radiation modes through the surrounding medium (such as the liquid analyte being sensed). The light from the microresonator 110 that is detected by the second detector 172 may be, for example, either scattered out of the microresonator 110 or may be fluorescence arising from excitation of a fluorescent species, near the surface of the microresonator, by light circulating within the microresonator 110. The second detector 172 may detect all wavelengths of light from the microresonator 110 or, for example, through the use of a wavelength selective element 174 placed between the second detector 172 and the microresonator 110, may detect light that lies in a specific wavelength range. The wavelength selective element 174 may, for example, be a filter that rejects light at the excitation wavelength resonating within the microresonator 110 and that transmits light at the fluorescent wavelength. The second detector 172 may also be used with a configuration like that shown in FIG. 1B. These microresonator devices of FIGS. 1A-1C are described to provide context for the description of the microresonator-waveguide coupling structures of the invention.

Configuration Examples for Coupling a Metal Clad Waveguide to a Microresonator

There are many different examples of how a metal clad waveguide can be coupled to a microresonator resulting in a microresonator structure with an acceptable amount of optical loss and a simpler manufacturing process than many other waveguide types.

Figure 3:
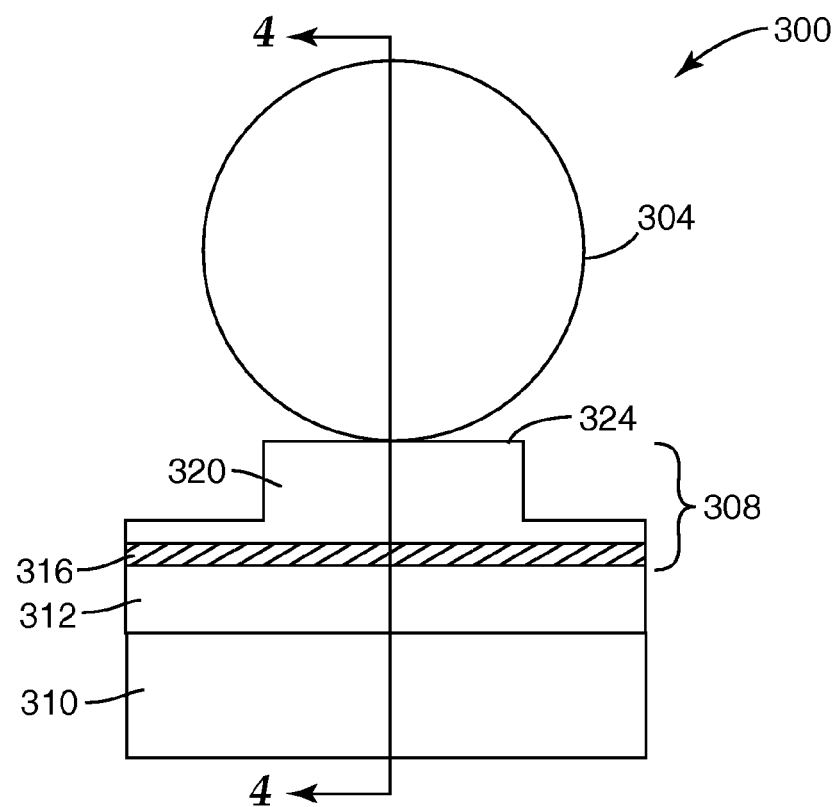
FIG. 3 schematically illustrates an embodiment of a metal-clad waveguide coupled to a spherical microresonator.
Figure 4:
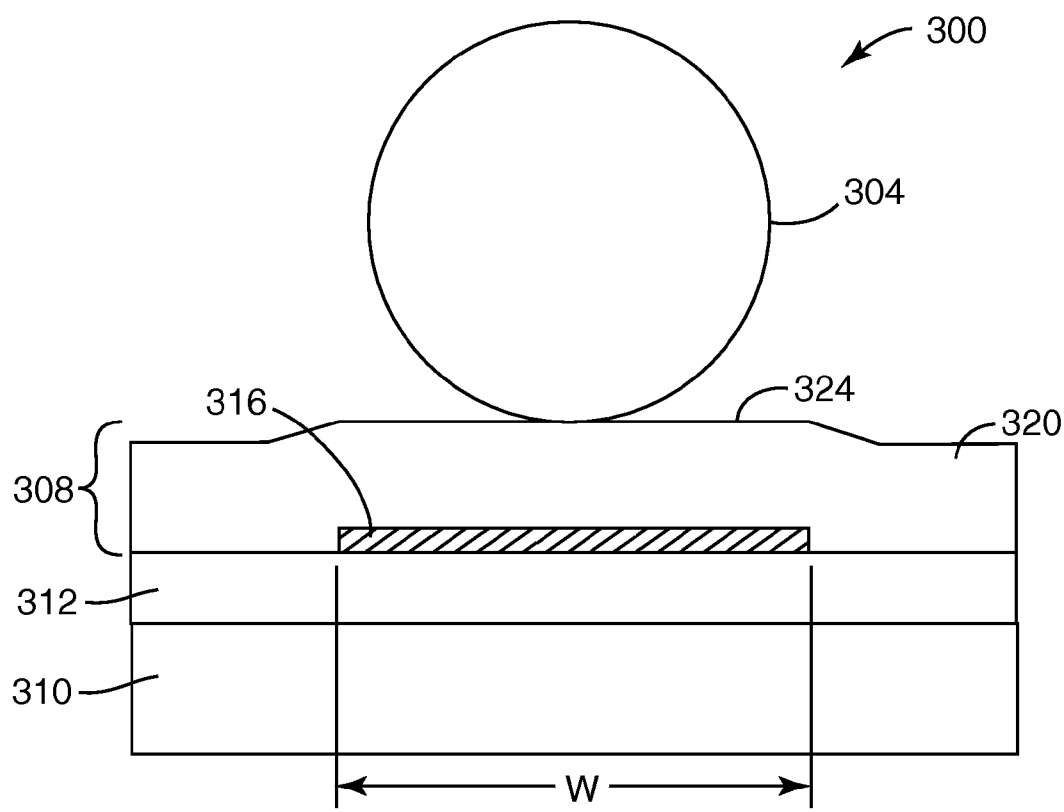
FIG. 4 schematically illustrates a lateral cross-section of the embodiment of FIG. 3 along the line 4-4.

One example of such a coupling is illustrated in FIGS. 3 and 4, where a microsphere-waveguide structure 300 includes a microsphere resonator 304 vertically coupled to a metal-clad optical waveguide 308. FIG. 4 is a cross-sectional view along line 4-4 in FIG. 3. Note that FIGS. 3 and 4 are not to scale, since the waveguide width is typically much smaller than the microsphere diameter, but the dimensions have been distorted here to allow depiction of both the sphere and the waveguide structural details. FIGS. 5-12 also are not to scale as the wave-guide width would typically be much smaller than the resonator size in those examples also. Metal-clad waveguide 308 is constructed on a substrate 310, which is a silicon wafer in this example. First, a dielectric cladding layer 312 of, for example, silica, is grown on the silicon wafer 310. Then, a metallic layer 316 is formed, followed by the growth of the dielectric core layer 320. The metallic layer 316 is chosen to serve as a reflective interface to prevent the light from penetrating into the substrate. In one embodiment, the core layer is silica. The core 320 is partially etched to form a core ridge 324. The dielectric core layer 320 has a higher refractive index than the dielectric cladding layer 312. The core's outer surfaces define boundaries and the metallic layer 316 is on at least a part of one boundary of the core. In the embodiment of FIGS. 3-4, the metallic layer is on a portion of the bottom side of the core 320 for the orientation shown in FIGS. 3-4.

In a variation of the above, the dielectric cladding layer may be omitted if the metal cladding will be present along the entire length of the waveguide. In that case, the metal would be deposited directly on the silicon wafer 310.

In one embodiment, the metallic layer is gold, with a thickness of 150 to 300 nanometers. In one embodiment, the width of the core ridge is about 4.6 μm. The thickness of the core layer may vary from 1 micron to 5 microns. Variations in the core layer thickness will achieve different coupling efficiencies, as will be demonstrated when simulation and experimental results are described below.

FIG. 4 is a cross-section view of the embodiment of FIG. 3, taken along the line 4-4 of FIG. 3. FIG. 4 illustrates that the metal cladding layer 316 is present only under the microresonator 304. Because the use of a metal cladding layer does increase the optical loss compared to dielectric cladding layers, the metal cladding layer 316 is only present in the vicinity of the microresonator in this embodiment. For example, in the embodiment of FIGS. 3-4, the length of the metal cladding layer in the direction of propagation is about 300 microns and the microsphere 304 has a diameter of 300 microns. The metal cladding layer 316 is centered with respect to the microsphere 304. In some embodiments, the width of the metal cladding layer (w in FIG. 4) ranges from 0.1 times the diameter of the microsphere to the length of the entire waveguide.

The channel waveguide structure 308 of FIGS. 3-4 is made monolithically on a planar substrate using semiconductor fabrication techniques. Then the microsphere is suspended above the surface of the channel, to produce a hybrid configuration where the optical coupling between the sphere and the waveguide takes place in the vertical direction. This approach preserves the high Q-factor of the glass microsphere, but does not solve the problem of how to precisely control the coupling between the microsphere and the waveguide. (Approaches to controlling the coupling between a microsphere and a channel waveguide have been proposed in U.S. Published Patent Application No. 2005/0077513.)

Some of the above issues related to coupling a microresonator to a waveguide can be overcome by abandoning the hybrid system based on the microsphere resonator, and using a fully-integrated system in which both the coupling waveguide(s) and the resonant cavity are fabricated via planar processing. In this case, the problems of the accuracy and stability of the positions of the waveguide and resonator are solved. However, it is still difficult to control coupling due to the small distance (approximately 100 to 300 nm) that the waveguide field projects outside the waveguide channel. The reason for the small extent of this "evanescent" field is the high index contrast required to achieve low loss in small resonators. As a result of the small extent of the evanescent field, good coupling between a waveguide and resonator necessitates that a very narrow gap be fabricated between them, generally less than 1 micron wide. Accurate and repeatable fabrication of such narrow gaps is very difficult, especially since the waveguide layers are typically several microns thick.

Examples will now be described where the entire microresonator-waveguide structure can be manufactured monolithically. This is possible when the resonant cavity is a disk or ring, or other resonant cavity based on a single mode channel or multimode planar waveguide rather than a sphere, so the microresonator and waveguide can be fabricated on the same planar substrate. This monolithic approach is typically realized in glass, polymer, or semiconductor waveguides, and provides excellent stability of coupling between the waveguides and the resonator. The etching processes used to fabricate the microresonator, however, invariably introduce surface roughness, that results in a scattering loss thereby degrading the Q of the cavity. Cavities formed using this approach typically have a Q-factor value of around a few thousand.

Figure 5:
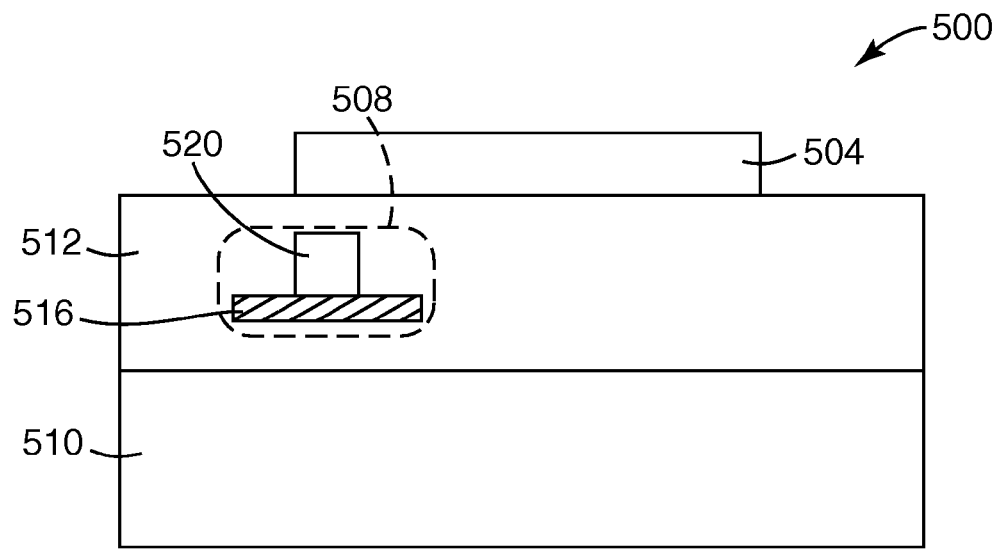
FIG. 5 schematically illustrates an embodiment of a planar (disk or ring) microresonator vertically coupled to a metal-clad waveguide.

FIG. 5 illustrates an embodiment of a microresonator-waveguide coupling system 500 including a disk or ring microresonator 504 that is vertically coupled to a metal-clad optical waveguide 508. Waveguide 508 is constructed on a substrate 510, which is a silicon wafer in this example. First, a dielectric cladding layer 512 of, for example, silica, is grown on the substrate 510. Next, a metal layer 516 is deposited and etched to provide a localized metal cladding region in the area where coupling to the resonator is desired. Next bus waveguide dielectric core layer 520 is deposited and patterned. The waveguide core is then buried under more of the dielectric cladding material 512, and optionally planarized. Finally, the higher-index core layer for the resonant cavity 504 is deposited and patterned. The core layer 520 has outer surfaces that define boundaries of the core. The metallic layer 516 is on at least a portion of the boundary of the core layer, in this case the bottom side of the core 520 for the orientation shown in FIG. 5. The metallic layer 516 serves as a highly reflective cladding that prevents the light from penetrating into the substrate, and forces the optical mode in the bus waveguide up towards the microresonator to enhance the coupling strength. In one embodiment, the core layer is also silica, with a dopant added to raise its refractive index. The bus waveguide core layer 520, and the resonant cavity layer 504 have higher refractive indices than the dielectric cladding layer 512.

Figure 6:
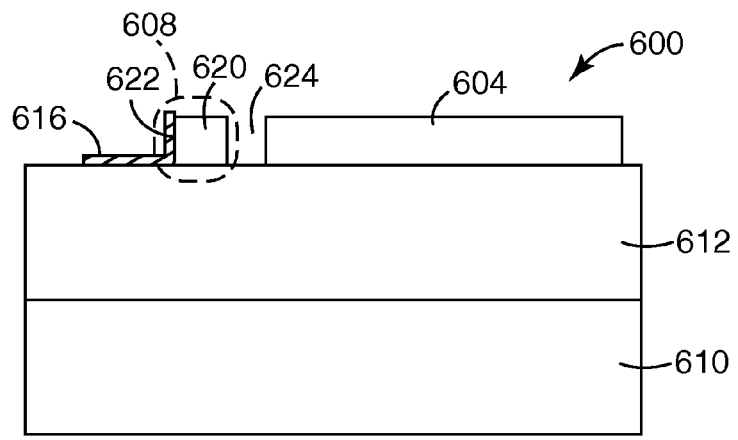
FIG. 6 schematically illustrates a planar microresonator laterally coupled to a metal-clad waveguide.

The example of FIG. 5 has the microresonator vertically coupled to the waveguide. It is also possible to have a lateral coupling relationship, as illustrated in FIG. 6 by microresonator-waveguide structure 600. A microresonator 604 formed as a ring or a disk is coupled to a metal clad waveguide 608. The waveguide 608 is grown on a substrate 610 and includes a dielectric cladding layer 612 and a bus waveguide core 620. Metal cladding 616 is positioned on the side 622 of the bus waveguide core 620 that is opposite from the microresonator 604. The metal cladding 616 is also positioned on the top of the dielectric cladding 612 that is immediately adjacent to the bus waveguide core 620. A gap 624 is present between the microresonator 604 and the bus waveguide core 620. The metal cladding 616 on the side 622 of the core serves to push the waveguide mode towards the resonator for enhanced coupling.

Figure 7:
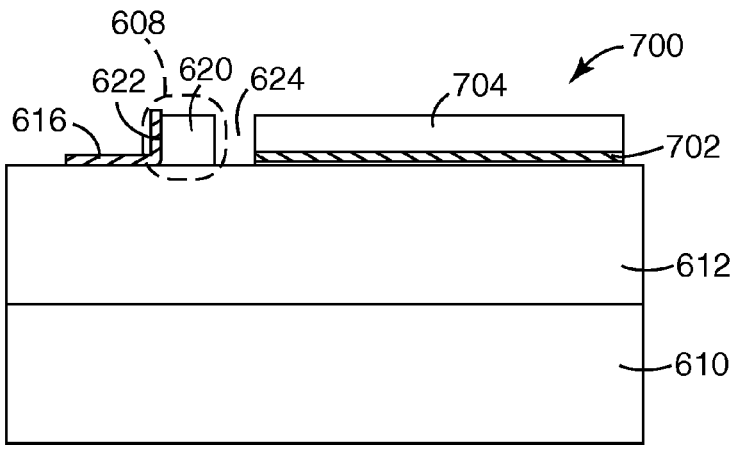
FIG. 7 schematically illustrates a planar microresonator laterally coupled to a metal-clad waveguide, with the resonator modified for greater surface sensitivity.

FIG. 7 illustrates a microresonator-waveguide coupling structure 700 that is nearly identical to FIG. 6, except that an additional metal cladding portion 702 is present directly beneath the microresonator core 704. In this configuration the optical mode in the resonator is pushed towards the top of the resonator, resulting in stronger electric field at the top surface, thus increasing the surface sensitivity of the microresonator. Note that this structure may result in larger optical loss than in other embodiments because the metal cladding is in contact with the resonator, but can be used in cases where achieving extremely high Q is not critical, or perhaps not even desirable, as in the case of fluorescence-based sensors. Identical reference numbers on FIGS. 6 and 7 indicate identical elements.

Figure 8:
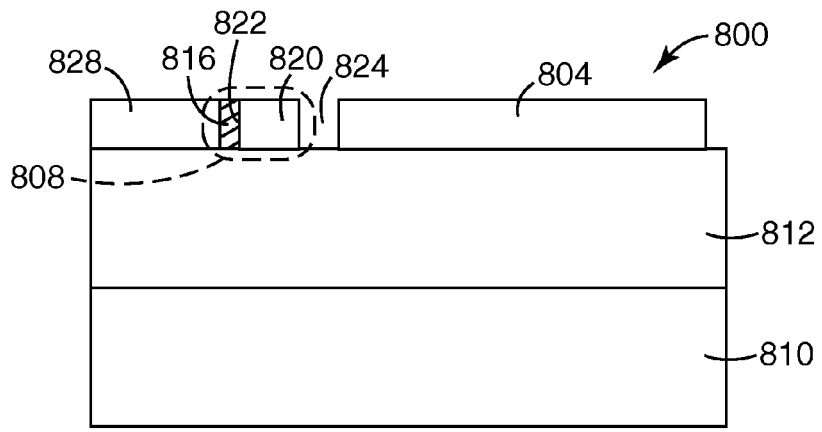
FIG. 8 schematically illustrates a planar microresonator laterally coupled to a metal-clad waveguide, with the metal cladding positioned in a gap to strengthen the waveguide.

FIG. 8 illustrates a microresonator-waveguide structure 800 with many similarities to the structure 600 of FIG. 6. A microresonator 804 formed as a ring or a disk is laterally coupled to a metal clad waveguide 808. The metal-clad waveguide 808 is grown on a substrate 810 and includes a dielectric cladding layer 812 and a bus waveguide core 820. The metal cladding 816 is positioned on the side 822 of the bus waveguide core 820 that is opposite from the microresonator 804. A gap 824 is present between the microresonator 804 and the bus waveguide core 820. A feature not present in FIG. 6 but illustrated in FIG. 8 is a reinforcement structure 828 adjacent to the metal cladding layer 816. The reinforcement structure 828 strengthens and supports the bus waveguide core 820 and metal layer 816, thereby improving reliability. In one example, the reinforcement structure 828 is the same material as the waveguide core 820.

Figure 9:
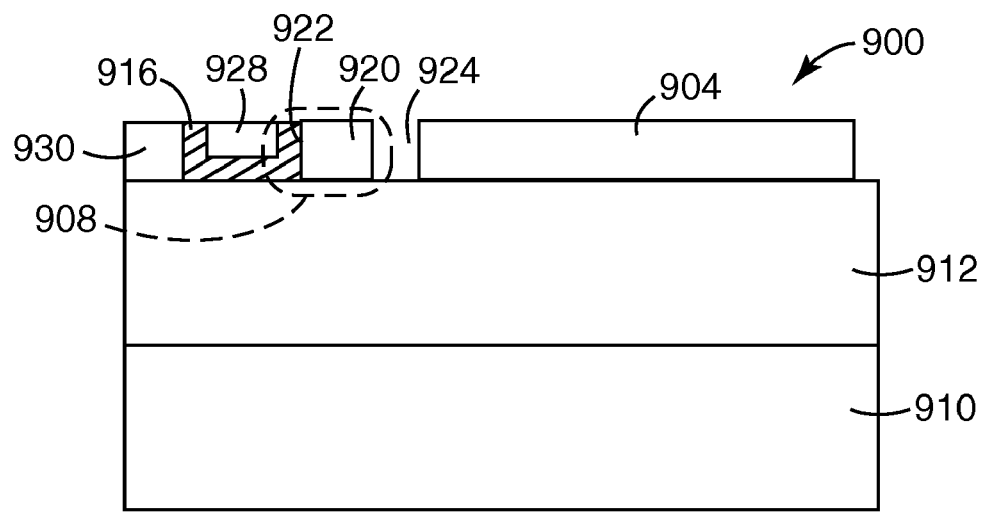
FIG. 9 schematically illustrates a planar microresonator laterally coupled to a metal-clad waveguide, with metal and dielectric cladding positioned in a gap to strengthen the waveguide.

FIG. 9 also illustrates a microresonator-waveguide structure 900 that includes a microresonator 904 formed as a ring or a disk that is laterally coupled to a metal clad waveguide 908. The waveguide 908 is fabricated on a substrate 910, and includes a dielectric cladding layer 912 and a bus waveguide core 920. The metal cladding 916 is positioned on the side 922 of the bus waveguide core 920 that is opposite from the microresonator 904, as well as on the top of the dielectric cladding 912 that is immediately adjacent to the bus waveguide core 920. The waveguide 908 also includes a reinforcement structure 928 that is surrounded by the metal cladding layer 916 on three sides. The reinforcement structure 928 strengthens and supports the bus waveguide core 920, thereby improving reliability. In one example, the reinforcement structure 928 is a dielectric material which provides more mechanical strength than the metal layer. In addition, a section 930 of the same material as the waveguide core is present adjacent to the metal cladding 916 to provide additional mechanical stability and thereby improve reliability.

Figure 10:
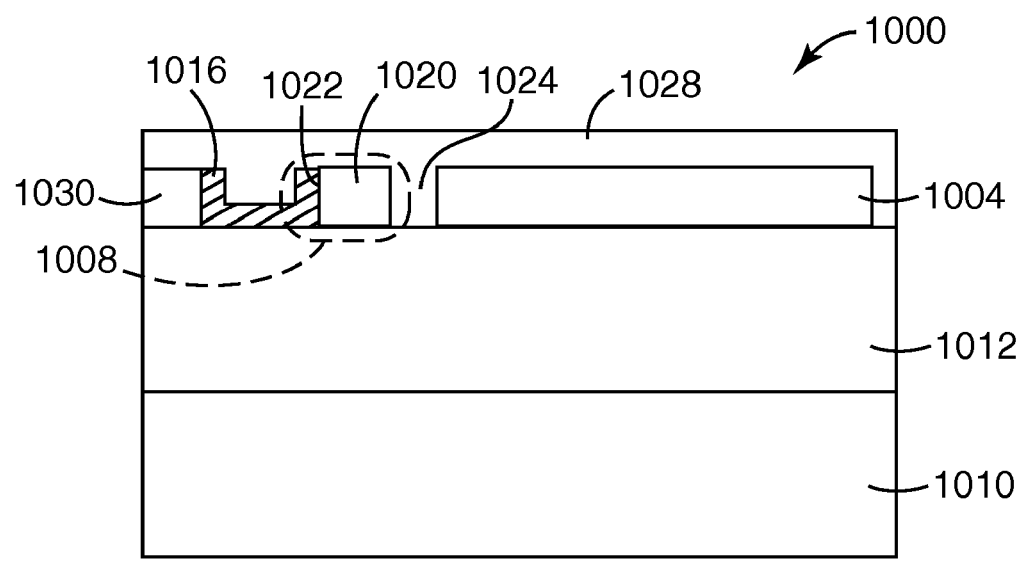
FIG. 10 schematically illustrates a planar microresonator laterally coupled to a metal-clad waveguide, with metal and dielectric cladding positioned in a gap to strengthen the waveguide and with dielectric cladding over the top of the structure to add additional strength FIG. 11 schematically illustrates three spherical microresonators vertically coupled to a metal-clad waveguide.

FIG. 10 illustrates a microresonator-waveguide structure 1000 nearly identical to the structure 900 of FIG. 9, laterally coupling a disk or ring microresonator 1004 and a waveguide 1008. However, a dielectric fill material 1028 is present not just adjacent to the metal cladding layer 1016, but also over the entire top surface of the structure 1000 and in the gap 1024 between a bus waveguide core 1020 and the microresonator 1004. The waveguide 1008 is fabricated on a substrate 1010 and includes a lower dielectric cladding layer 1012. The waveguide 1008 includes a portion 1030 of waveguide core material for added stability for the waveguide and metal structures. The dielectric fill structure 1028 provides a relatively low cost technique to mechanically reinforce the microresonator, waveguide core 1020, and metal cladding 1016 structures. Additionally, because the index of the fill material 1028 is higher than that of air, the optical confinement in the waveguide will be weakened, and the coupling between the resonator and waveguide will be enhanced. In order to allow the microresonator-waveguide structure 1000 to be used as a sensor, the dielectric fill material 1028 is permeable to liquid or gases so that an analyte can move through the dielectric fill material 1008 to reach the microresonator 1004. In an alternate approach, the fill material is designed to have the correct refractive index and thickness so that the resonator field will penetrate to its top surface and therefore be available for coupling to an analyte at the top surface of the fill material 1028.

Figure 11:
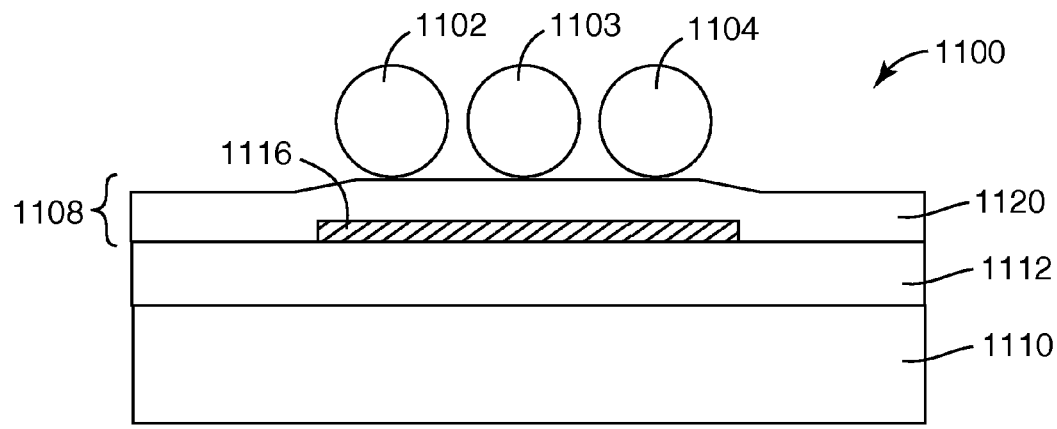

FIG. 11 illustrates a microresonator-waveguide structure 1100 with three microsphere resonators 1102, 1103, 1104 that are coupled in a hybrid fashion to a single channel waveguide 1108. The structure 1100 includes a substrate 1110, a dielectric cladding layer 1112 and a waveguide core 1120. A single metal cladding layer section 1116 is positioned beneath a portion of the waveguide core 1120 and the three microresonators 1102, 1103, 1104. At the boundaries of the metal layer, reflections are expected that may in some cases interfere with the desired operation of the resonators, so it is desirable to group the three microresonators over one metal cladding layer, thereby eliminating the occurrence of multiple reflections. Of course, any number of resonators could be coupled to the same metal-clad core in this way.

Figure 12:
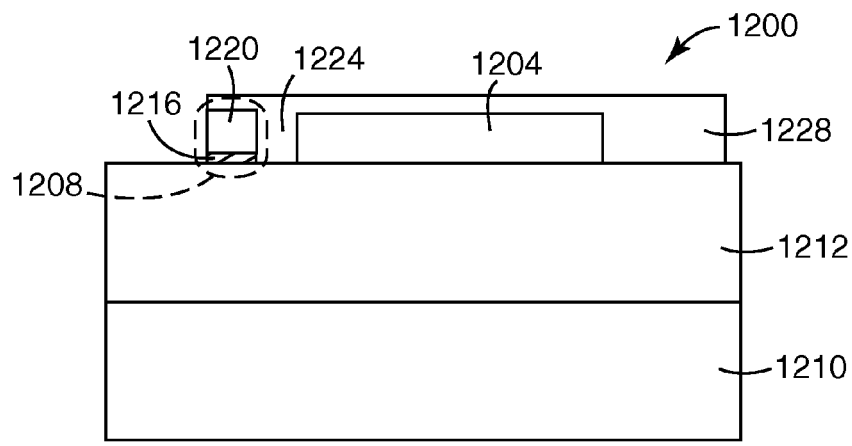
FIG. 12 schematically illustrates a planar microresonator laterally coupled to a metal-clad waveguide, with metal positioned under the waveguide core.

FIG. 12 illustrates a microresonator-waveguide structure 1200 where metal cladding 1216 under a waveguide core 1220 causes the field to be pushed into the upper cladding 1228 on the resonator side, thus improving the coupling. The structure 1200 includes a disk or ring microresonator 1204 laterally coupled to the waveguide 1208. A structure having metal cladding 1216 under the waveguide core is easier to fabricate than a structure with metal cladding on the side of the waveguide core.

In FIG. 12, the dielectric fill material 1228 is present as the top surface of the structure 1200 and in the gap 1224 between a bus waveguide core 1220 and the microresonator 1204. The waveguide 1208 is fabricated on a substrate 1210 and includes a lower dielectric cladding layer 1212. The dielectric fill structure 1228 provides a relatively low cost technique to mechanically reinforce the microresonator and waveguide core 1220. Additionally, because the index of the fill material 1228 is higher than that of air, the optical confinement in the waveguide will be weakened, and the coupling between the resonator and waveguide will be enhanced. In order to allow the microresonator-waveguide structure 1200 to be used as a sensor, the dielectric fill material 1228 is permeable to liquid or gases so that an analyte can move through the dielectric fill material 1228 to reach the microresonator 1204. In an alternate approach, the fill material is designed to have the correct refractive index and thickness so that the resonator field will penetrate to its top surface and therefore be available for coupling to an analyte.

Microresonator Features

The microresonator typically has a diameter in the range from 10 µm to five millimeters, but is more often in the range 10 µm-500 µm. The microresonator may be a ring resonator, a sphere resonator, a toroidal resonator, a disk resonator, a racetrack resonator, a rectangular resonator, a polygonal shape resonator, or a Fabry-Perot cavity resonator. A common diameter for a microsphere resonator is 300 µm, whereas resonators made by planar fabrication technologies can be made much smaller.

In some embodiments, the surface of the microresonator is modified for greater surface sensitivity. For example, commonly-owned U.S. Publication No. 2005/0078731 describes porous microsphere resonators that increase the amount of material that can be introduced to the surface of a microresonator that has whispering gallery modes.

General Waveguide Features

The waveguide is often tapered to increase the intensity of the optical field outside the waveguide, thus increasing the amount of light that couples into the microresonator. In the case of an optical fiber waveguide, the fiber may be heated and tapered by stretching, or may be chemically etched to a total thickness of about 1-5 µm. Likewise, with a planar or channel waveguide, the waveguide core thickness or width may be reduced at the region where the light is coupled to the microresonator. In addition to the waveguide being reduced in size, the thickness of the cladding around the waveguide may also be reduced.

A stable relative position between the microresonator and a waveguide taper can be difficult to achieve. Various approaches to establishing stable relative positions of the microresonator and the waveguide are discussed in greater detail in commonly owned and co-pending U.S. Published Patent Application No. 2005/0077513, incorporated herein by reference.

Where a waveguide includes a core ridge, there are many options for positioning a metal cladding layer relative to the core ridge. In one embodiment, the metal coating is located beneath the core ridge. In another embodiment, the metal cladding layer is beneath at least a part of the core ridge. In yet another embodiment, the metal cladding layer is on at least a part of the side of the core ridge.

In one embodiment, the waveguide core includes one or more of the following materials: silica, silicon, silicon nitride, silicon oxynitride, titania, zirconia, Group III-V compound semiconductor, Group II-VI compound semiconductor, and polymer. The silica material can have a dopant, such as germanium, phosphorous, or titanium in the silica.

The metal layer may be any metal which acts as a good reflector in the optical frequency range in which the device is to be operated. That is, the imaginary part of the refractive index should be large, typically greater than 5. However, in order to further achieve low propagation loss, high magnitudes of the ratio of the imaginary part of the refractive index to the real part of the refractive index are desirable, generally such that k/n is greater than 5.

Table I provides values for optical constants n and k for several metals, measured at a wavelength of either 633 nm or 1550 nm, or both. Table I also shows the ratio k/n for some metals. In addition, Table I shows the skin depth for each metal at 1550 nm. The skin depth is calculated as follows:

$$\text{Skin depth} = \frac{0.08 * 1550 \text{ nm}}{\sqrt{(n*k)}}$$

It is important to be aware that measurements of optical constants for metals can vary depending on the particular material sample, the measurement techniques, and other factors. As a result, the values in Table I may differ from optical constant values found from other sources.

TABLE I

Optical Constants for Some Metals of Potential Interest for Waveguide Cladding

| | Wavelength (nm) | | | | | | |
|---|---|---|---|---|---|---|---|
| Metal | 633 n | 633 k | 633 k/n | 1550 n | 1500 k | 1500 k/n | 1550 Skin Depth (nm) |
| Aluminum | 1.4 | 7.7 | 5.5 | 1.44 | 16 | 11.1 | 26 |
| Cobalt | | | | 4.5 | 5.8 | 1.29 | 24 |
| Copper | 0.21 | 3.7 | 18 | 0.61 | 8.3 | 13.6 | 55 |
| Gold | 0.17 | 3.2 | 19 | 0.56 | 11.5 | 20.5 | 49 |
| Indium | | | | 2.3 | 11.3 | 4.91 | 24 |
| Iridium | 2.53 | 4.6 | 1.8 | 3.14 | 8.61 | 2.74 | 24 |
| Iron | | | | 4.1 | 5.6 | 1.37 | 26 |
| Lead | | | | 1.67 | 8.24 | 4.93 | 33 |
| Magnesium | 0.48 | 3.7 | 7.7 | 2.04 | 8.6 | 4.22 | 30 |
| Molybdenum | 3.71 | 3.6 | 1 | 1.64 | 7.75 | 4.73 | 35 |
| Nickel | 1.98 | 3.7 | 1.9 | 3.38 | 6.82 | 2.02 | 26 |
| Niobium | 2.52 | 2.5 | 1 | 2.3 | 6.6 | 2.87 | 32 |
| Osmium | 3.88 | 1.7 | 0.4 | 2.00 | 5.95 | 2.98 | 36 |
| Platinum | 2.3 | 4.1 | 1.8 | 5.44 | 7.08 | 1.3 | 20 |
| Rhenium | 3.41 | 3.1 | 0.9 | 4.37 | 8.3 | 1.9 | 21 |
| Rhodium | 2.12 | 5.5 | 2.6 | 3.63 | 10.3 | 2.84 | 20 |
| Silver | 0.14 | 4.2 | 30 | 0.51 | 10.8 | 21.2 | 53 |
| Sodium | 0.03 | 2.6 | 87 | 0.45 | 9 | 20 | 62 |
| Strontium | 0.61 | 2.1 | 3.4 | 2 | 6.7 | 3.35 | 34 |
| Tantalum | 2.13 | 2.9 | 1.4 | 1.85 | 6.1 | 3.3 | 37 |
| Vanadium | | | | 2 | 5.4 | 2.7 | 38 |
| Ytterbium | 0.78 | 3.3 | 4.2 | 1.63 | 6.1 | 3.74 | 39 |
| Zinc | 3.25 | 4.3 | 1.3 | 1.47 | 6.97 | 4.74 | 39 |

Metals which are acceptable for the cladding layer include aluminum, gold, indium, silver, rhodium, sodium, iridium, magnesium, copper, rhenium, lead, molybdenum, platinum, zinc, nickel, strontium, niobium, tantalum, ytterbium, osmium, cobalt, iron, vanadium and alloys of these elements. Gold, silver, aluminum, copper, and alloys thereof are particularly useful as metal cladding layers at 1550 nm wavelength, due to the lower loss of waveguides based on them.

These metals are selected to balance the field enhancement benefits against the optical loss. The total optical loss to the microresonator device caused by the addition of the metal cladding will depend on how long a region of the waveguide is coated with metal for coupling, which depends in turn on the size of the resonator. The coupling region will range from 10 to 100 microns in length in many embodiments. Choosing the longest value, 100 microns, to estimate a minimum for the attenuation/mm, it is reasonable to define "low loss" as less than 10 dB/mm. Essentially any of the metals listed herein will work if loss of 100 dB/mm is acceptable, corresponding to 1 dB in a 10 micron length. To some degree, the definition of low loss and acceptable loss is arbitrary, because the amount of loss that can be tolerated is a system level issue that depends on how much power is available, how strong the signal is, noise sources, and other factors.

Of course, the field enhancement and attenuation are wavelength dependent, so the choice of metal will depend on the operating wavelength. Based on calculations, the following trends emerge:

1) When k is >5 for the operating wavelength, most of the field enhancement is achieved.

There is some benefit for k down to 2 or so, but the best performance required k>5.

2) When k/n is >5, the loss is predicted to be less than 10 dB/mm.

These principles can be applied to commonly used wavelengths of interest: 1550 nm and 633 nm. The list of metals that will provide good field enhancement at an operation wavelength of 1550 nm is as follows: aluminum, gold, indium, silver, rhodium, sodium, iridium, magnesium, copper, rhenium, lead, molybdenum, platinum, zinc, nickel, strontium, niobium, tantalum, ytterbium, osmium, cobalt, iron, and vanadium. For loss <10 dB/mm, the list becomes: gold, silver, aluminum, sodium and copper. Obviously, for chemistry reasons, sodium would not be easy to use. At an operating wavelength of 633 nm, the list of metals that will provide good field enhancement is aluminum and rhodium. Of those, only aluminum also gives loss less than 10 dB/mm.

In some embodiments, the metal cladding layer is patterned. In some embodiments, the dielectric cladding layer is patterned. The thickness requirement on the metal layer is determined by the depth of the electric field penetration into the metal, described by the skin depth (1/e decay length for the electric field). For optimal performance in metal clad waveguides where the intent is to enhance coupling, the metal should be thick enough that no significant electric field penetrates to the side of the metal opposite the core. At an operating wavelength of 1550 nm, the skin depths for typical metals are between 20 and 50 nm. In order to limit the optical mode to one side of the metal, a thickness exceeding about two skin depths is desirable. Therefore, depending upon the properties of the metal, a minimum thickness between 40 and 100 nm is appropriate. Note however that beyond exceeding the minimum thickness, control of the exact thickness of the metal is not required. Where the thickness of the metal is at least greater than twice the skin depth at the wavelength of operation, the result is that less than 2% of the optical power is on the wrong side of the metal, opposite the core.

A graded transition on a substrate is present in some embodiments between a conventional waveguide and the metal clad waveguide. The metal clad waveguide in one example is an optical fiber taper with a metal cladding layer on one side of the taper.

Method of Assembling a Coupling of a Channel Waveguide to a Microresonator

As mentioned previously, there are two primary categories of methods for assembling a coupling of a metal clad channel waveguide to a microresonator: hybrid and monolithic. In both approaches, a first substrate is provided, on which is fabricated a waveguide, where the waveguide comprises a core and a metal cladding layer on at least a portion of one side. Then a microresonator is positioned so that the microresonator is in an optically coupling relationship with the waveguide. The two options are that the waveguide and resonator are fabricated as a monolithic integrated optical circuit, or the waveguide and resonator are fabricated separately and are then assembled as a hybrid optical circuit.

Advantages of Metal Clad Waveguides Over ARROW Structures

Non-fiber wave guides, such as integrated optical channel waveguides, have not found general use with microsphere resonators because of the difficulty in making the optical field available outside of the waveguide sufficiently large to obtain adequate coupling of the light into the microsphere. One example of channel waveguide structure that has been used with microspheres is known as the Anti-Resonant Reflecting Optical Waveguide (ARROW). A more specific type of ARROW is a Stripline Pedestal Anti-Resonant Reflecting Optical Waveguide (SPARROW). ARROW structures optically isolate the waveguide core from the substrate with a high-reflectivity stack of alternating high- and low-index layers of materials, such as Si and $SiO_2$, the thicknesses of which are defined as a quarter of the vertically directed guide wavelength. An early document describing ARROW structures is U.S. Pat. No. 4,715,672 to Duguay et al. U.S. Pat. No. 6,657,731 to Tapalian et al describes the use of SPARROW waveguides for coupling light into a microresonator in a chemical sensor. A disadvantage of ARROW structures is that they include multiple layers requiring thickness control during fabrication, and are therefore quite time consuming and complex to manufacture.

A metal-clad waveguide is very simple to manufacture compared to an ARROW structure. Rather than growing multiple layers of alternating high and low index material, a simple single layer of metal may be used according to the present invention. In addition, ARROW structures require fairly accurate control of the reflector layer thickness, while the metal cladding layer of the present invention only need be thicker than some minimum value without adversely affecting the performance of the structure.

It is very difficult to make a graded on-chip transition between a conventional waveguide and a ARROW. However, because of the smaller thickness of the metal layer, it is easier to make a graded on-chip transition between a conventional waveguide and a metal clad waveguide. It is also easier to apply a metal coating on the side of a ridge waveguide than it is to deposit a multilayer reflector there, in order to enhance lateral coupling, as shown in FIGS. 6-10.

Modeling and Experimental Results

A series of modeling experiments were performed to determine the typical characteristics of a metal clad waveguide. To this end, an analytical approach was used as well as commercially available Beam Propagation Method (BPM) software to solve for effective modal indices, field amplitudes, and propagation losses for various metal clad waveguide structures. Specifically, BeamPROP™ software was used as the BPM software, which is available from RSoft Design Group, Inc. of Ossining, N.Y.

One goal of the modeling experiments was to determine the fraction of the waveguide electric field amplitude outside of the core on the side where the resonator is positioned. It is believed that this value is important because it is related to the strength of coupling between the waveguide mode and resonator modes. The Relative Field Increase is defined as the ratio of this integrated amplitude for the specified construction to that for a reference construction.

The analytical approach was used to look for general trends by studying the characteristics of a metal-clad slab waveguide structure (see Kaminow et al, Metal-Clad Optical Waveguides Analytical and Experimental Study, Applied Optics v 13, p 396 (1974)). The structure consisted of three layers: an infinitely thick metal layer; a 1 micron thick core layer with a refractive index of 1.5; and an infinitely thick top dielectric cladding layer with a refractive index of 1.33. The reference construction was identical except for a 1.45 index layer in place of the metal layer. The Relative Field Increase in the top cladding layer and the calculated attenuation for wavelengths of 633 nm and 1550 nm are shown in FIGS. 13A-C and 14A-C.

Figure 13A:
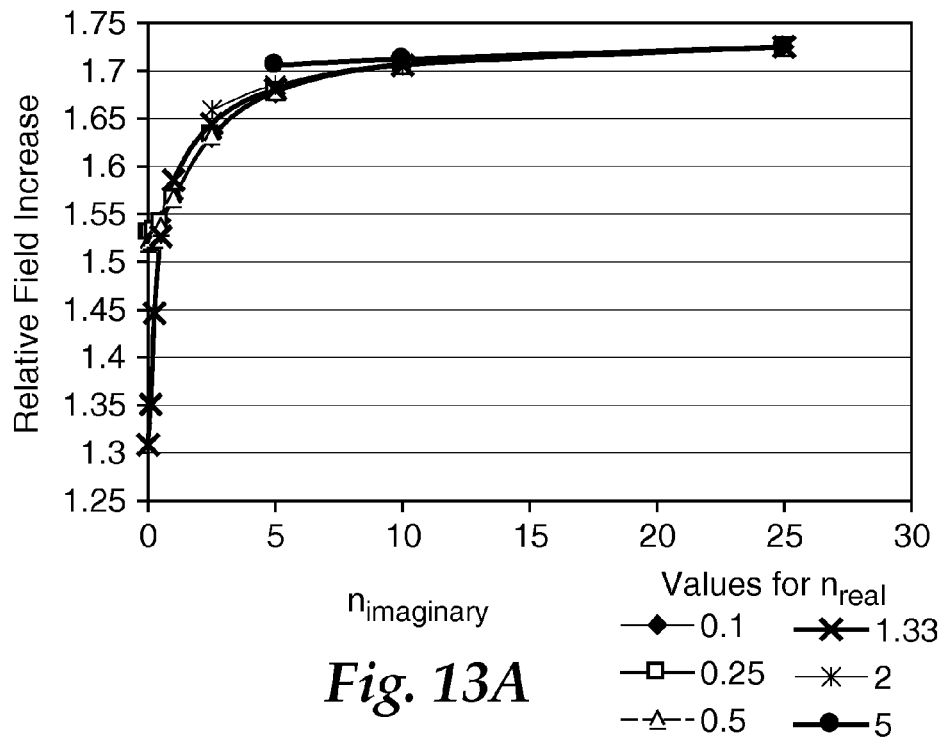
FIGS. 13A, B and C show modeling results for an example slab waveguide structure, showing the effect of the real and imaginary index of the metal cladding on the relative field enhancement and the waveguide attenuation for a wavelength of 633 nm.

FIG. 13A shows the Relative Field Increase at the top cladding layer plotted against the imaginary portion of the index of refraction of the metal, for six different values of the real portion of the index of refraction of the metal, for a wavelength of 633 nm.

Figure 13B:
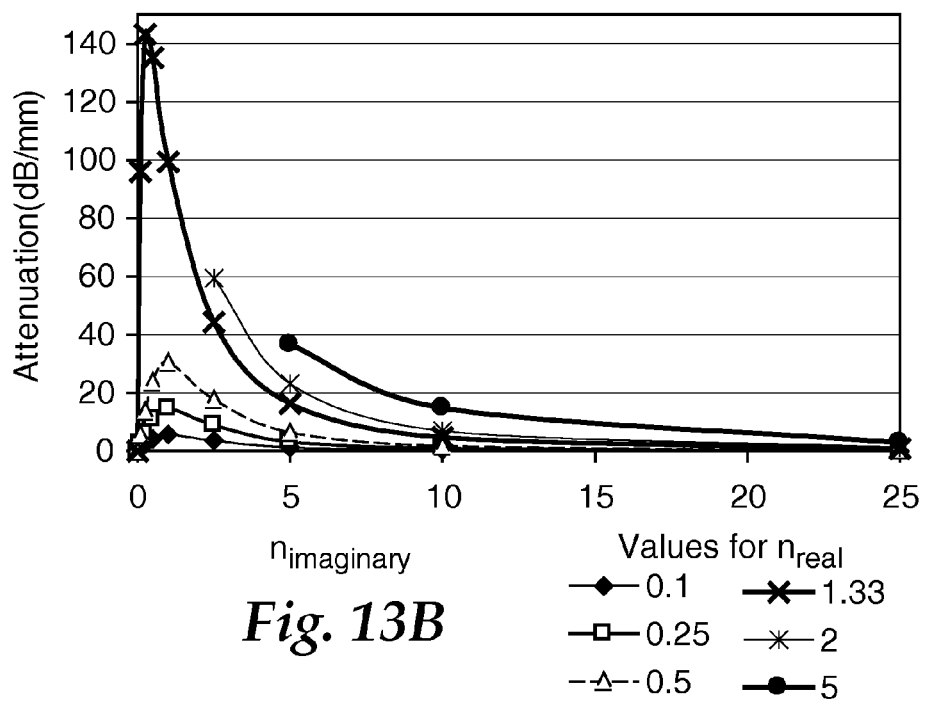
Figure 13C:
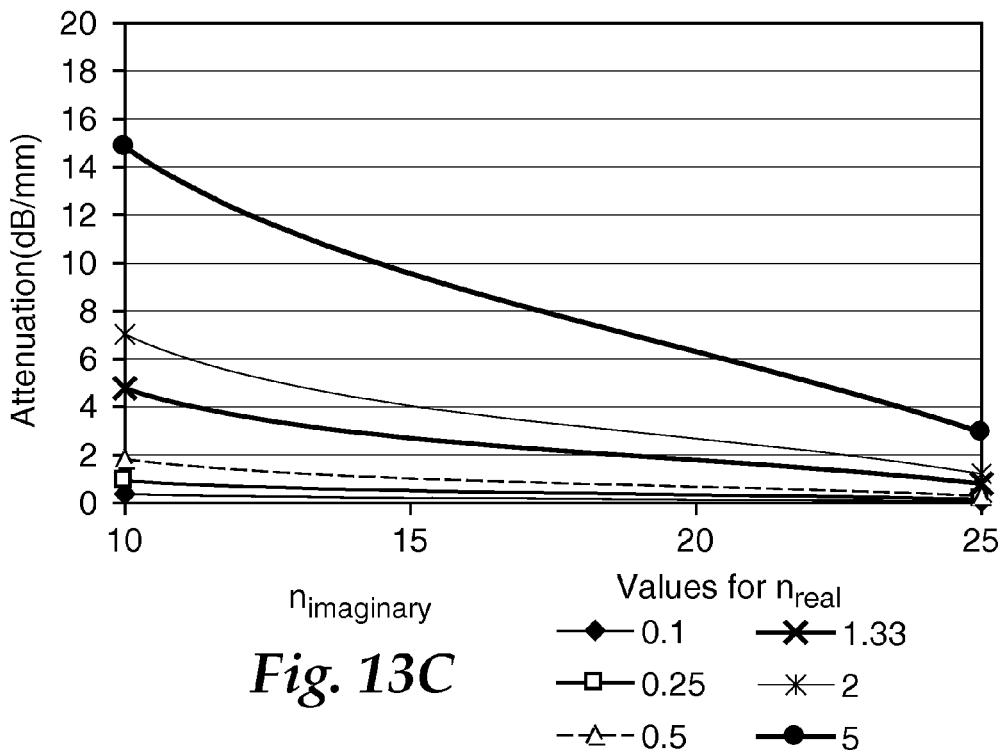

FIGS. 13B and 13C show the Attenuation of TE0 polarized light in units of decibels per millimeter at a wavelength of 633 nm plotted against the imaginary portion of the index of refraction of the metal, for six different values of the real portion of the index of refraction of the metal. FIG. 13C shows the same data as FIG. 13B, but using a finer scale for both axes.

Figure 14A:
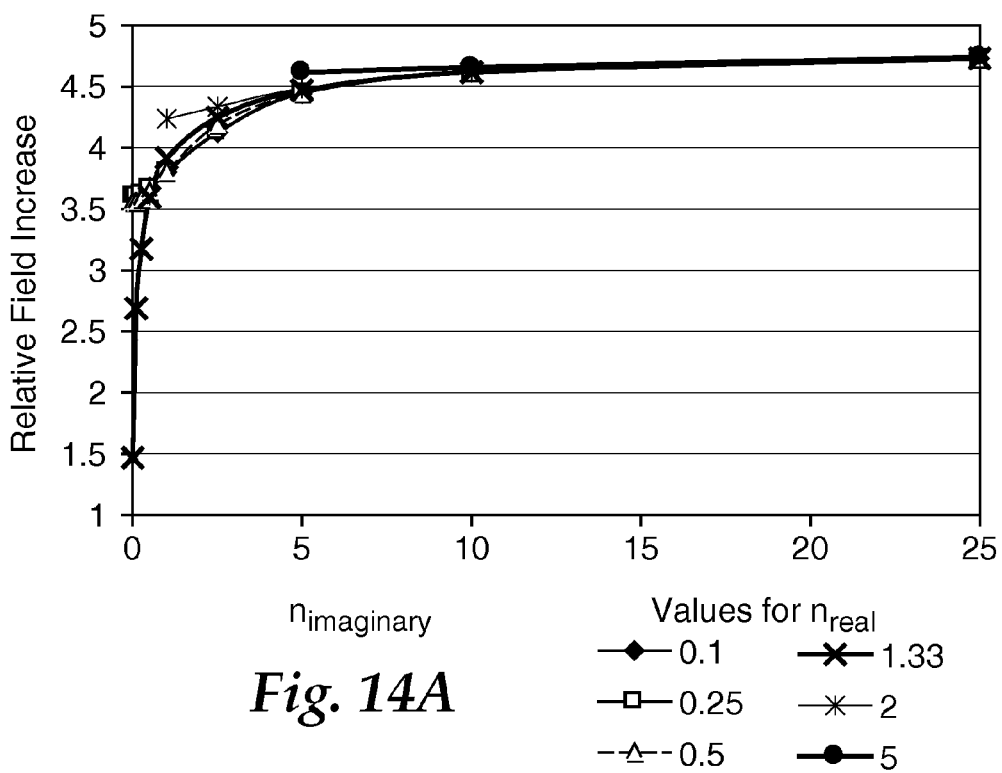
FIGS. 14A, B and C show modeling results for an example slab waveguide structure, showing the effect of the real and imaginary index of the metal cladding on the relative field enhancement, and the waveguide attenuation for a wavelength of 1550 nm.
Figure 14B:
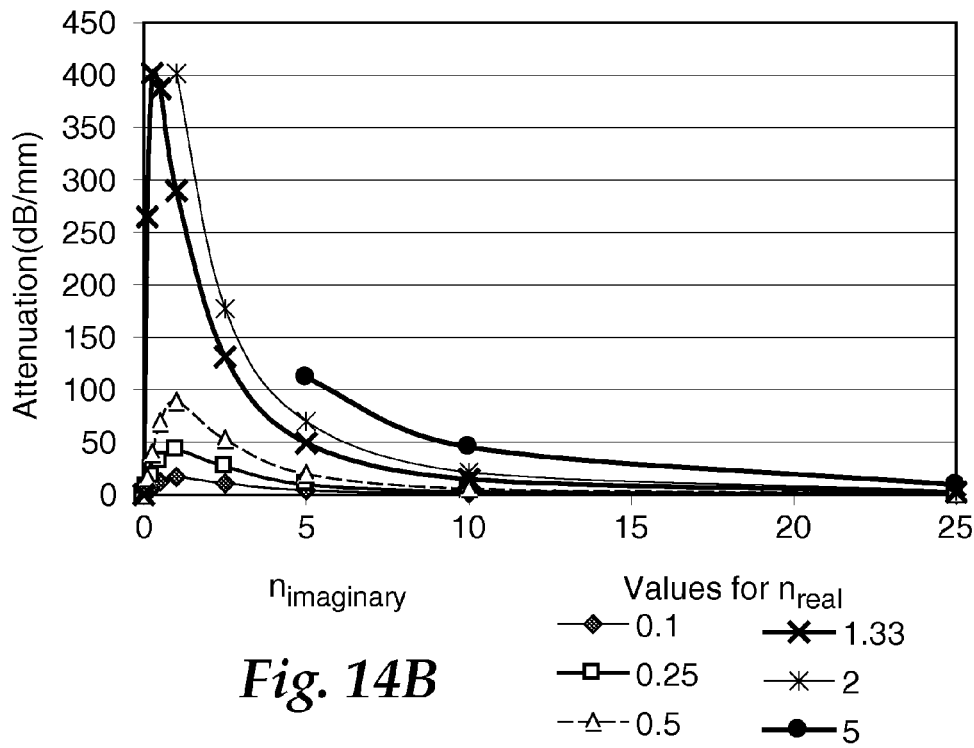
Figure 14C:
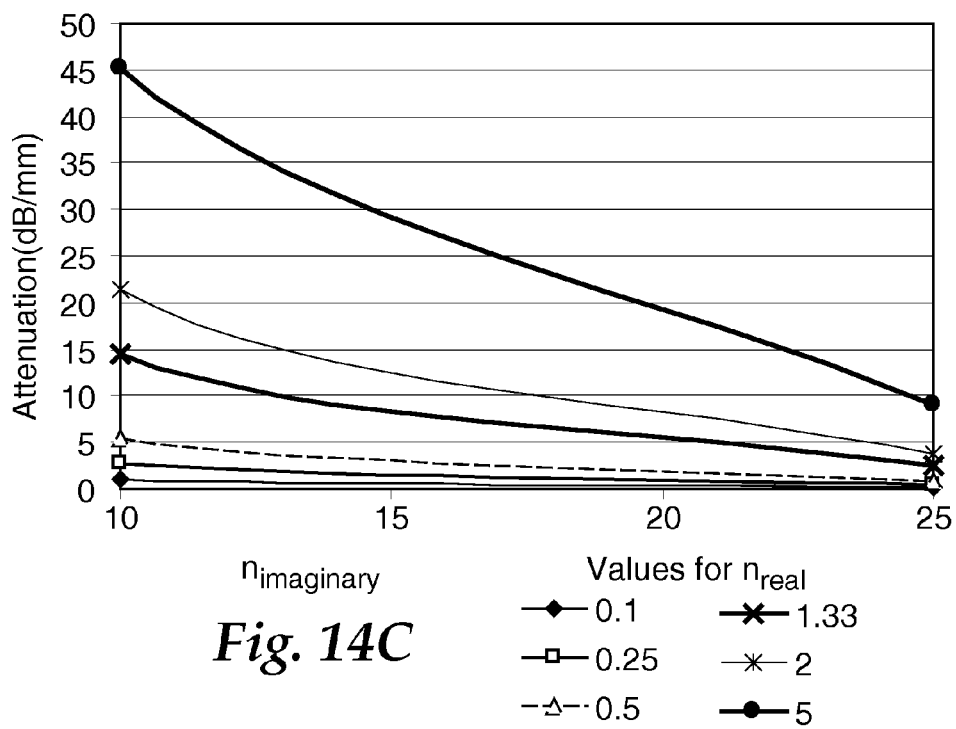

FIG. 14A shows the Relative Field Increase at the top cladding layer plotted against the imaginary portion of the index of refraction of the metal, for six different values of the real portion of the index of refraction of the metal for a wavelength of 1550 nm. FIGS. 14B and 14C show the Attenuation of TE0 polarized light in units of decibels per millimeter at a wavelength of 1550 nm plotted against the imaginary portion of the index of refraction of the metal, for six different values of the real portion of the index of refraction of the metal. FIG. 14C shows the same data as FIG. 14B, but using a finer scale for both axes.

Figure 15:
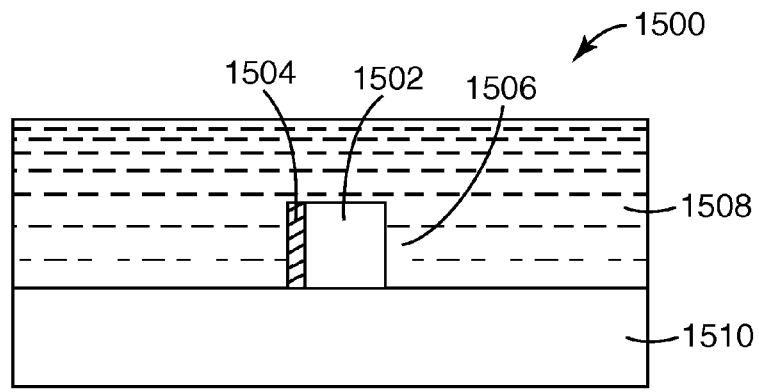
FIG. 15 illustrates a channel waveguide configuration for which numerical modeling was performed, the results of which are shown in FIGS. 16-18.

Numerical modeling using beam propagation software was done to assess the benefits of the metal cladding in realistic channel waveguide configurations (as opposed to the slab waveguide configurations for which the analyses are easily performed analytically). FIG. 15 illustrates the channel waveguide configuration 1500 for which the numerical modeling was performed.

The channel waveguide structure included a core 1502, and the core had a width and height of 1.5 and 2 microns, respectively, and the index of refraction was 1.53. The starting refractive index and thickness for the metal layer 1504 was 0.56+i11.5 and 200 nm, respectively. From this starting point, the thickness and imaginary index of the metal was varied to look for dependencies. The core 1502 sits upon a silica substrate 1510, having an index of 1.45. An upper cladding 1508 is water with an index of refraction of 1.33. The Relative Field Increase was measured in the right clad region 1506. For all cases, the wavelength was 1550 nm. The reference construction for the Relative Field Increase calculation is the case with no metal. As a result, the index of what would be the metal region in the other models is 1.33 for the reference constructon.

With the metal clad structure of FIG. 15, the intention is to increase the amount of electric field in the water clad region on the right side of the core compared to the reference construction.

Figure 16:
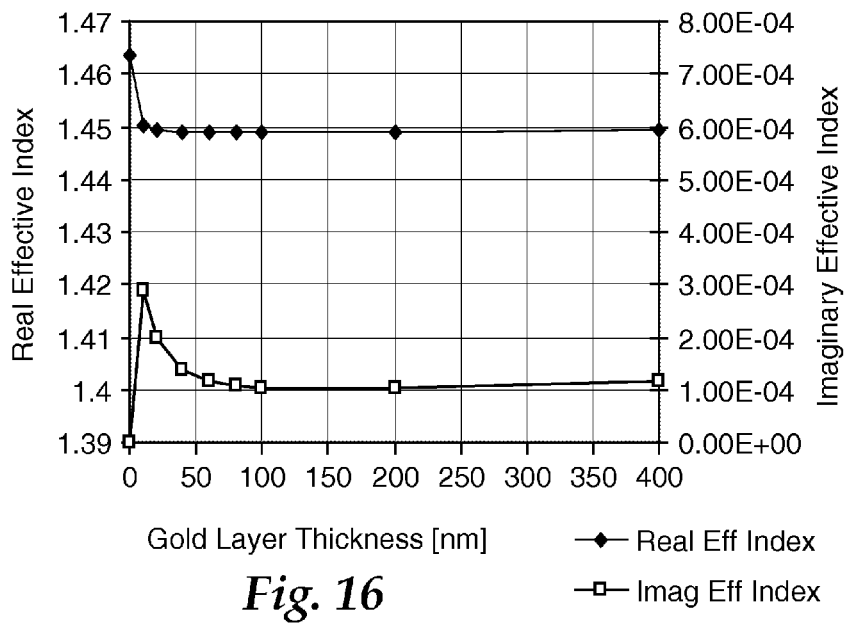
FIG. 16 shows a Beam Propagation Method (BPM) calculation of the dependence of the effective modal index on the thickness of the metal layer in FIG. 15, for a wavelength of 1550 nm, where the metal is gold.
Figure 17:
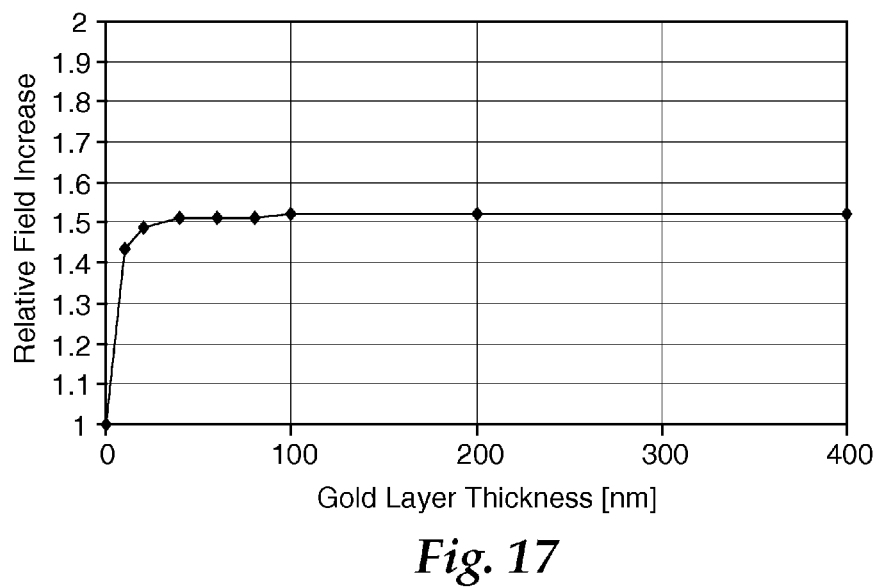
FIG. 17 shows a BPM calculation of the relative field enhancement for the metal-clad waveguide shown in FIG. 15, as a function of the thickness of the metal layer.

FIG. 16 graphs the dependence of the real and imaginary propagation constant on gold layer thickness for the example channel waveguide structure shown in FIG. 15. FIG. 17 illustrates the Relative Field Increase in the right clad region for the example channel waveguide structure shown in FIG. 15, for varying gold layer thicknesses.

FIGS. 16 and 17 demonstrate that for the example structure of FIG. 15, a relatively thin layer of metal could be used. For example, the metal layer thickness in one embodiment is greater than 20 nm. In another embodiment, the metal layer thickness is greater than 40 nm. In yet another embodiment, the thickness of the metal cladding is greater than 50 nm. For another embodiment, the thickness of the metal cladding layer is greater than 80 nm. For metal cladding layer thicknesses of greater than 50 nm, the structure will avoid losses and leakage of the mode through the metal cladding that may occur with thinner metal layers. The actual thickness of metal required for a given structure will depend upon waveguide type, geometry and layer refractive indices, as well as the metal used and the wavelength of operation.

Figure 18:
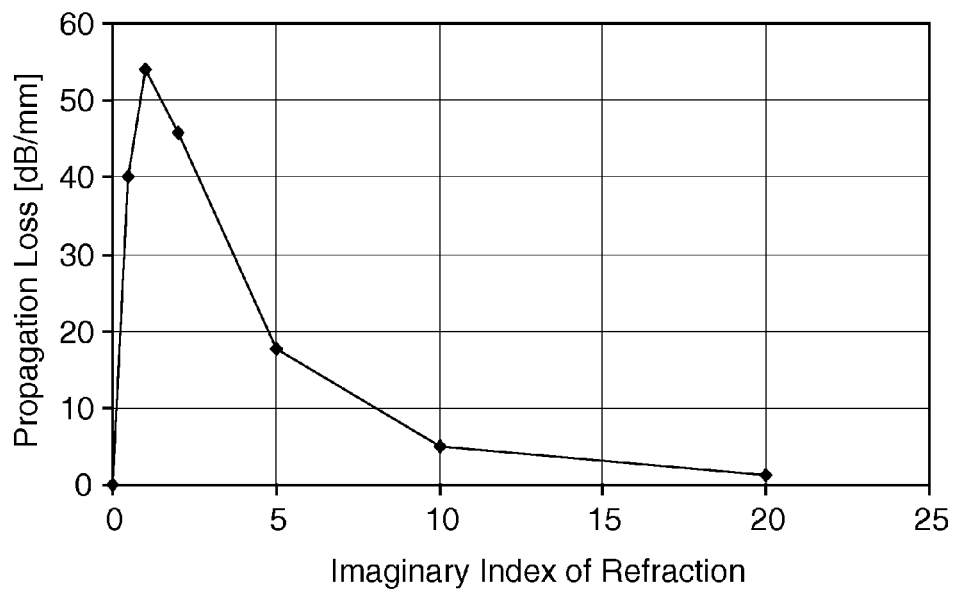
FIG. 18 shows a BPM calculation of the propagation loss for the metal-clad waveguide shown in FIG. 15, as a function of the imaginary index of the metal.

FIG. 18 shows the propagation loss for the example structure shown in FIG. 15, while varying the metal imaginary index of refraction and holding the real part of the index of refraction to 0.56. Results from FIG. 18 agree very well with the results from the analytical model shown in FIG. 14B, for the case where the real part of the index of refraction was 0.5.

Experiments were carried out to determine the observed Q-factors of microresonators coupled to a metal-clad waveguide. The observed quality factor is defined by $Q_{obs} = 2\pi \upsilon_0 \tau$ where $\upsilon_0$ is the resonant frequency and $1/\tau$ is the cavity decay rate for a particular mode. It is determined experimentally using the relation $$Q_{obs} = \frac{\lambda_0}{\Delta\lambda_0}$$

where $\lambda_0$ and $\Delta\lambda_0$ are the resonance wavelength and ½ width respectively.

Also, $$\frac{1}{Q_{obs}} = \frac{1}{Q_{int}} + \frac{1}{Q_{coup}}$$

where $Q_{int}$ is the intrinsic quality factor of the resonator and $Q_{coup}$ is the contribution due to coupling to the waveguide. The fraction of light transmitted through the waveguide is measurable and equals $$\frac{P_{trans}}{P_{inc}} = \left(1 - \frac{2Q_{obs}}{Q_{coup}}\right)^2$$

Notice that the maximum light intensity will be extracted from the waveguide when $$Q_{coup} = Q_{int}$$

Rearranging gives $$Q_{coup} = \frac{2Q_{obs}}{1 \pm \sqrt{P_{trans}/P_{inc}}}$$

and $$\frac{1}{Q_{int}} = \frac{1}{Q_{obs}} - \frac{1}{Q_{coup}}$$

The example tested was that of FIGS. 3 and 4, where the microsphere resonator had a diameter of 300 microns and the waveguide included a gold cladding layer with a thickness of 300 nm. The waveguide's core thickness was varied for different experiments. The width of the core ridge was 4.6 microns. The experimental arrangement was similar to that shown in FIG. 1A. In each experiment, a gold-clad waveguide 108 was placed in contact with the microresonator 110 and both were immersed in water. A tunable diode laser was used as light source 102 with the laser wavelength at 980 nm. The wavelength of the light emitted by the laser was tuned by varying the voltage that drives a piezo-actuator inside the laser. When the wavelength was on-resonance with one or more of the whispering gallery modes 112 of the microresonator, the amount of laser power coupled into the microresonator was increased, leading to a power drop at the detector 106.

Figure 19:
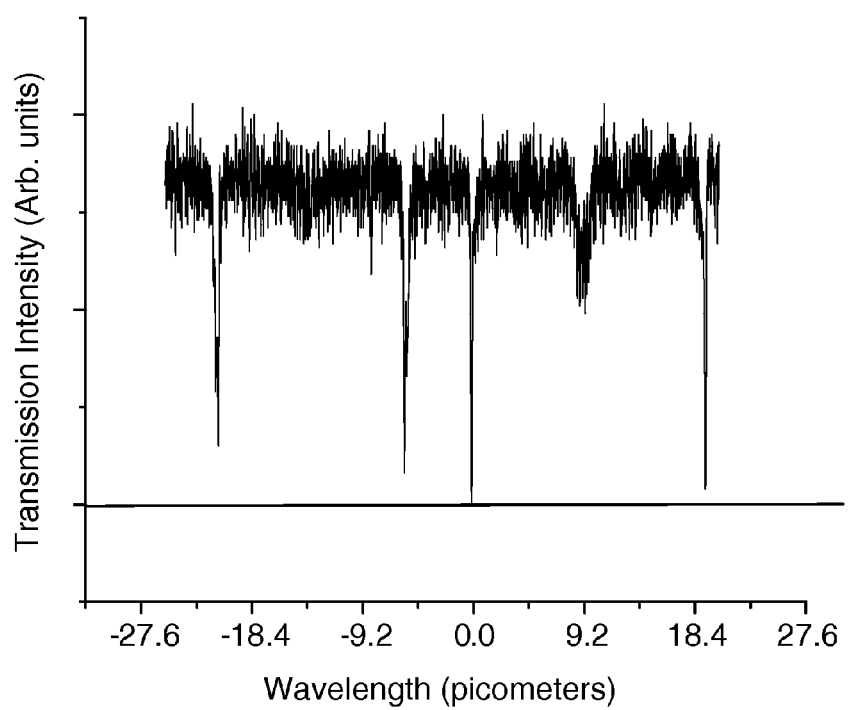
FIG. 19 is a graph showing experimentally obtained resonance plots for an embodiment of microresonator consisting of a microsphere coupled to a metal-clad waveguide, in accordance with principles of the invention.

FIG. 19 shows the detected signal at the detector as a function of laser tuning, where the core thickness was 2.0 micron thick. The observed Q-factor of the microresonator was estimated from these results to be approximately $7 \times 10^6$ and the efficiency was nearly 100%. The intrinsic Q factor of the microresonator resonator was calculated to be $1.4 \times 10^7$.

This result confirms that microresonators with high Q-factors can be effectively coupled to a metal-clad waveguide.

In a different experiment, the core thickness was 2.5 microns thick. The Q-factor of the microresonator system was approximately $3 \times 10^6$ and coupling efficiency was 78%. Another experiment was performed where the core thickness was 3 microns thick. The Q-factor of the microresonator system was approximately $1.5 \times 10^6$ and coupling efficiency was nearly 60%. In another experiment, the core thickness was 4 microns thick. The Q-factor of the microresonator system was approximately $5 \times 10^6$ and coupling efficiency was 30%.

During these experiments, it was found that the light attenuation or loss in the gold-clad waveguide coupled with the microsphere resonator was comparable to that of ARROW-structured waveguides. In addition, it was found that the gold-clad waveguide transmits only TE polarized light.

As noted above, the present invention is applicable to microresonators, and is believed to be particularly useful where microresonators are used in sensing applications. The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the present specification. The claims are intended to cover such modifications and devices.

The above specification provides a complete description of the structure and use of the invention. Since many of the embodiments of the invention can be made without parting from the spirit and scope of the invention, the invention resides in the claims.

We claim:

1. An optical microresonator device, comprising:
   an optical waveguide, wherein the waveguide comprises a core and a metal cladding layer on at least a part of one boundary of the core; and
   an optical microresonator positioned so as to optically couple to the waveguide.

2. The microresonator device of claim 1, wherein the optical microresonator is selected from the group consisting of a sphere resonator, toroid resonator, a ring resonator, a disk resonator, a racetrack resonator, a rectangular resonator, a polygonal shape resonator, and a Fabry-Perot cavity resonator.

3. The microresonator device of claim 1, wherein the optical waveguide core is a dielectric ridge positioned on a substrate.

4. The microresonator device of claim 3, wherein the metal cladding layer is beneath at least a part of the optical waveguide core ridge.

5. The microresonator device of claim 3, wherein the metal cladding layer is on at least a part of a boundary of the optical waveguide core ridge that is opposite from the position of the microresonator.

6. The microresonator device of claim 1, wherein the waveguide core is comprised of silica.

7. The microresonator device of claim 1, wherein the waveguide core is selected from a group consisting of silicon, silicon nitride, silicon oxynitride, titania, zirconia, Group III-V compound semiconductor, Group II-VI compound semiconductor, and polymer.

8. The microresonator device of claim 1, wherein the metal cladding layer is selected from a group consisting of aluminum, gold, indium, silver, rhodium, sodium, iridium, magnesium, copper, rhenium, lead, molybdenum, platinum, zinc, nickel, strontium, niobium, tantalum, ytterbium, osmium, cobalt, iron, vanadium, and alloys of these metals.

9. The microresonator device of claim 1, wherein the metal cladding layer is selected from a group consisting of gold, silver, aluminum, copper and alloys thereof.

10. The microresonator device of claim 1, wherein the metal cladding layer has a thickness that exceeds two times the skin depth of the metal at the operating wavelength.

11. The microresonator device of claim 1, further comprising a substrate upon which the waveguide and microresonator are both positioned.

12. The microresonator device of claim 1, further comprising at least one transition between a dielectric-clad waveguide and the metal-clad waveguide.

13. The microresonator device of claim 1, wherein the metal cladding layer is present on the waveguide core only along a section of core proximate to the resonator.

14. The microresonator device of claim 1, wherein the waveguide is an optical fiber comprising an optical fiber taper with the metal cladding layer on a boundary of the taper opposite from the resonator.

15. The microresonator device of claim 11, wherein the waveguide is laterally-coupled to the microresonator.

16. The microresonator device of claim 11, wherein the waveguide is vertically coupled to the microresonator.

17. An optical microresonator device, comprising:
   an optical waveguide, comprising:
      a dielectric core, wherein the core includes a ridge, and
      a metal cladding layer on at least a part of one boundary of the core,
         wherein the metal cladding layer has a thickness that exceeds two times the skin depth of the metal at the operating wavelength; and
   an optical microresonator positioned so as to optically couple to the waveguide;
   wherein the metal cladding layer is on at least a part of a first side of the optical waveguide core ridge and the microresonator is positioned on a second, opposite side of the core ridge;
   wherein the metal cladding layer is present on the waveguide core only along a section of core proximate to the resonator.

* * * * *

UNITED STATES PATENT AND TRADEMARK OFFICE
CERTIFICATE OF CORRECTION

PATENT NO. : 7,389,025 B2  Page 1 of 1
APPLICATION NO. : 11/277769
DATED : June 17, 2008
INVENTOR(S) : Terry L. Smith It is certified that error appears in the above-identified patent and that said Letters Patent is hereby corrected as shown below:

On Page 2, Column 1, under (Other Publications)
Line 23, delete "Scieice" and insert -- Science --, therefor.

On Page 2, Column 2, under (Other Publications)
Line 1, delete "in" and insert -- on --, therefor.
Line 10, delete "Optical" and insert -- Optics --, therefor.
Line 12, delete "Optical" and insert -- Optics --, therefor.
Line 18, delete "Resonantor" and insert -- Resonator --, therefor.
Line 26, after "Applied" delete "of".
Line 48, before "than" insert -- More --.

On Page 3, Column 1, under (Other Publications)
Line 18, delete "Dieletric" and insert -- Dielectric --, therefor.

Column 14
Line 56, after "Waveguides" insert -- : --.

Signed and Sealed this

Twenty-first Day of October, 2008

JON W. DUDAS
*Director of the United States Patent and Trademark Office*